United States Patent
Gauthier et al.

(10) Patent No.: US 12,275,506 B2
(45) Date of Patent: Apr. 15, 2025

(54) AUTOMATED RECREATIONAL CLOSED CIRCUIT BREATHING DEVICE

(71) Applicant: Tesseron Ltd., Key Largo, FL (US)

(72) Inventors: Forrest P. Gauthier, Homestead, FL (US); Jeffrey E. Bozanic, Fountain Valley, CA (US)

(73) Assignee: Tesseron Ltd., Key Largo, FL (US)

( * ) Notice: Subject to any disclaimer, the term of this patent is extended or adjusted under 35 U.S.C. 154(b) by 558 days.

(21) Appl. No.: 16/458,539

(22) Filed: Jul. 1, 2019

(65) Prior Publication Data

US 2020/0001956 A1 Jan. 2, 2020

Related U.S. Application Data

(60) Provisional application No. 62/693,337, filed on Jul. 2, 2018.

(51) Int. Cl.
| | |
|---|---|
| *B63C 11/24* | (2006.01) |
| *A62B 7/14* | (2006.01) |
| *B63C 11/12* | (2006.01) |
| *B63C 11/16* | (2006.01) |
| *B63C 11/22* | (2006.01) |
| *A61M 16/06* | (2006.01) |
| *A62B 7/08* | (2006.01) |
| *A62B 7/12* | (2006.01) |

(52) U.S. Cl.
CPC ............... *B63C 11/24* (2013.01); *A62B 7/14* (2013.01); *B63C 11/12* (2013.01); *B63C 11/16* (2013.01); *B63C 11/22* (2013.01); *A61M 16/06* (2013.01); *A62B 7/08* (2013.01); *A62B 7/12* (2013.01); *B63C 2011/121* (2013.01)

(58) Field of Classification Search
CPC ......... B63C 11/00; B63C 11/02; B63C 11/12; B63C 11/18; B63C 11/22; B63C 11/24; B63C 11/26; B63C 2011/021; B63C 2011/022; B63C 2011/121; B63C 2011/188
See application file for complete search history.

(56) References Cited

U.S. PATENT DOCUMENTS

| | | | | |
|---|---|---|---|---|
| 3,995,626 A * | 12/1976 | Pearce, Jr. | ............... | A62B 9/02 |
| | | | | 128/205.24 |
| 4,781,184 A * | 11/1988 | Fife | ............ | A62B 7/10 |
| | | | | 128/205.12 |
| 5,195,516 A * | 3/1993 | Grimsey | ................. | B63C 11/24 |
| | | | | 128/205.12 |
| 5,485,834 A * | 1/1996 | Joye | ........................ | A62B 19/00 |
| | | | | 128/204.26 |
| 5,964,221 A * | 10/1999 | McKenna | .............. | B01D 53/62 |
| | | | | 128/201.27 |
| 6,712,071 B1 * | 3/2004 | Parker | ..................... | B63C 11/24 |
| | | | | 128/203.14 |
| 9,567,047 B2 * | 2/2017 | Gurr | ........................ | B63C 11/24 |
| 9,619,767 B2 * | 4/2017 | Braun | ................... | G06Q 50/265 |
| 2002/0106618 A1 * | 8/2002 | Ishida | ..................... | A63B 69/10 |
| | | | | 434/247 |
| 2004/0130504 A1 * | 7/2004 | Ebersole, Jr. | .......... | A62B 18/04 |
| | | | | 345/8 |
| 2006/0201508 A1 * | 9/2006 | Forsyth | ................... | B63C 11/22 |
| | | | | 128/204.26 |
| 2008/0105260 A1 * | 5/2008 | Heesch | ................. | A61M 16/01 |
| | | | | 128/205.28 |
| 2008/0216836 A1 * | 9/2008 | Ottestad | ................... | B63C 11/24 |
| | | | | 128/205.24 |
| 2009/0188501 A1 * | 7/2009 | Forsyth | .................... | B63C 11/24 |
| | | | | 128/204.22 |
| 2009/0188503 A1 * | 7/2009 | Brandt | ..................... | B63C 11/22 |
| | | | | 128/205.12 |
| 2010/0242966 A1 * | 9/2010 | Johnson | ................... | B63C 11/24 |
| | | | | 128/205.12 |
| 2017/0100610 A1 * | 4/2017 | Gurr | ........................ | A62B 7/02 |
| 2018/0074489 A1 * | 3/2018 | Buttet | .................. | G05D 1/0038 |
| 2021/0161404 A1 * | 6/2021 | Assouad | ............ | A61B 5/14551 |

OTHER PUBLICATIONS

Open Safety, Apocalypse Type IV Rebreather User Manual. copyright 2009 (Year: 2009).*

* cited by examiner

*Primary Examiner* — Colin W Stuart
(74) *Attorney, Agent, or Firm* — MacMillan, Sobanski & Todd, LLC

(57) ABSTRACT

A highly automated, fully-closed circuit rebreather and methods for operating the device by users with limited training and limited skill development are disclosed. Advanced sensors, electronics, software, assembly methods, and disposable cartridges dramatically reduce the skills required for assembly, operation, and maintenance of the unit. The use of the rebreather apparatus is primarily for recreational diving applications, but may be used for additional applications where the presence of breathable air may be absent or limited, such as hazardous duty applications, high altitude applications, no-atmosphere or low-atmosphere applications, and the like.

14 Claims, 19 Drawing Sheets

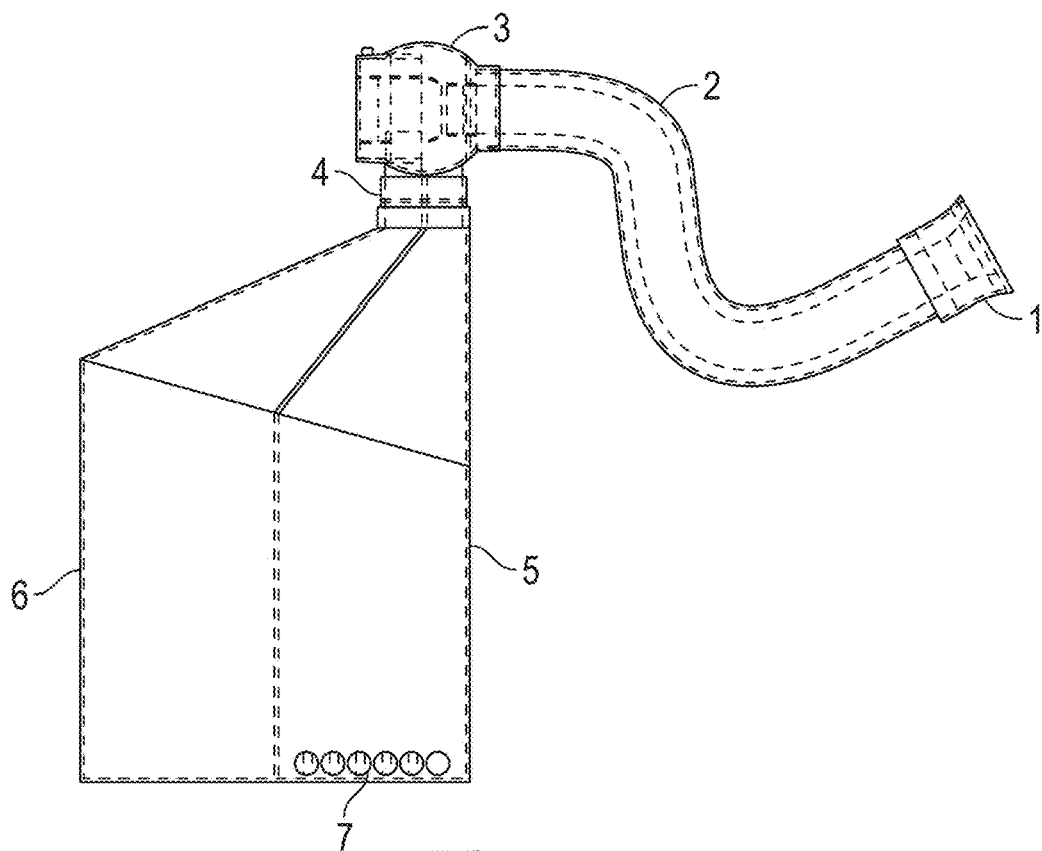
FIG. 3
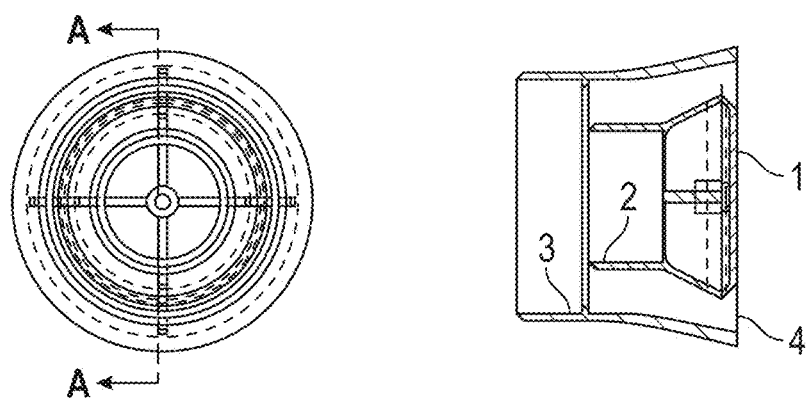
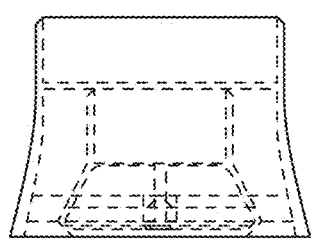
SECTION A-A
SCALE 2:1
FIG. 4

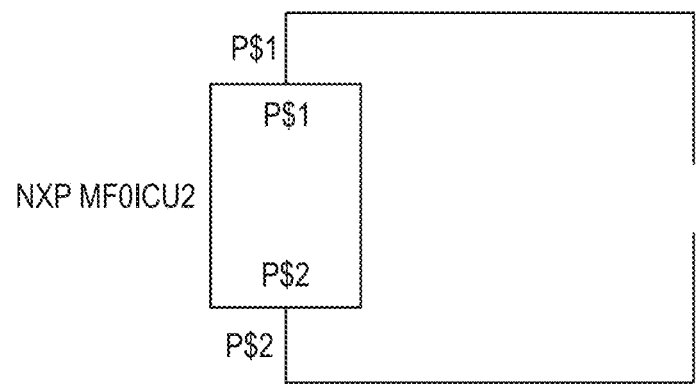
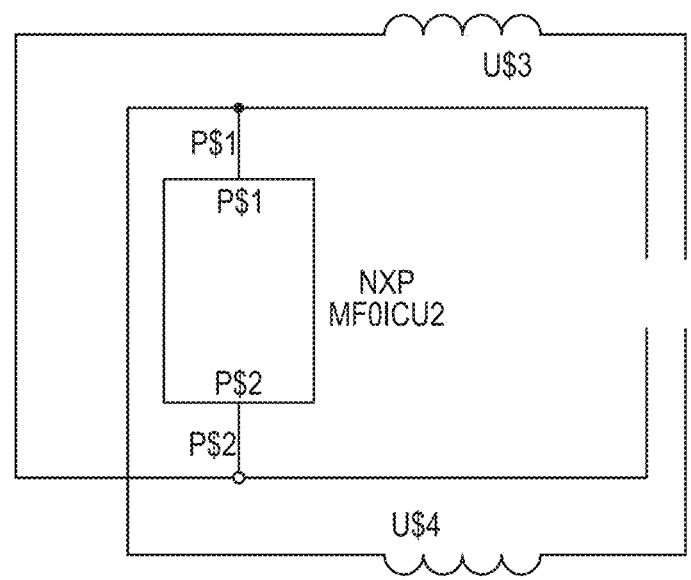
FIG. 29

AUTOMATED RECREATIONAL CLOSED CIRCUIT BREATHING DEVICE

CROSS-REFERENCE TO RELATED APPLICATIONS

This application claims the benefit of U.S. Provisional Application No. 62/693,337, filed Jul. 2, 2018, the disclosure of which is incorporated herein by reference.

BACKGROUND OF THE INVENTION

The present disclosure relates to apparatuses and methods for an automated closed circuit respiration device.

Open-circuit diving apparatuses are characterized by a supply cylinder of breathing gas, which cylinder is filled with compressed air or another mix of breathing gas, and a one-level or two-level pressure reducer, which reduces the pressure of the gas in the cylinder to ambient pressure. The exhaled air is emitted in the water, and only a small fraction of the oxygen in the breathing gas is metabolized by the body. Thus, at the water surface, about 3% of inhaled gas is used (25 liter breathing minute volume, 0.8 liter used oxygen, at rest), and at a further depth, for example 20 m, this value drops to ⅓ of such use or 1% inhaled gas, due to the 2 bar increased ambient pressure. Consequently, for a diving operation at 20 m, 100 times more volume of breathing gas must be carried along than what is actually metabolized by the user.

In order to avoid the low efficiency of breathing gas usage and mixture, which is inherent in open-circuit diving apparatuses, semi-closed circuit and fully-closed circuit rebreathers are employed. In these apparatuses, breathing is done in a fully-closed or semi-closed loop. Exhaled air in these apparatuses is cleaned from carbon dioxide by means of a carbon dioxide scrubber, then enriched with oxygen. Such apparatuses are further characterized by a one-part or two-part counter-lung, which can receive and store the exhaled gas volumes, then return the cleaned and enriched gas to the user on the inhale. With rebreathers, the efficiency regarding gas usage can be improved to up to 100%, and the gas mixture optimized during use.

Current art rebreathing devices disclose many devices and methods of rebreather design, carbon dioxide scrubber design, system controls, user interfaces, and manual and electronic device monitoring. Current art rebreathing devices often disclose the risks of using the device and discuss the need for significant user training of the device for proper assembly, operation, and maintenance.

SUMMARY OF THE INVENTION

The present disclosure concerns novel apparatus designs and methods of a highly automated, fully-closed circuit rebreather and methods for operating the device by users with limited training and limited skill development. Advanced sensors, electronics, software, assembly methods, and disposable cartridges dramatically reduce the skills required for assembly, operation, and maintenance of the unit. While the current disclosure describes use of the rebreather apparatus primarily for recreational diving applications, those having ordinary skill will understand that certain aspects of the embodiments described herein may be used for additional applications where the presence of breathable air may be absent or limited, such as hazardous duty applications, high altitude applications, no-atmosphere or low-atmosphere applications, and the like.

The present disclosure teaches a novel apparatus, design, and method of a highly automated fully closed circuit breathing device for recreational diving. The disclosed embodiment, the Pneuma Lung (Lung), is a highly automated device designed to be self-training and fail-safe when used as designed. It is not designed to be a replacement or competitive with technical, industrial, or military closed-circuit rebreathers. Rather, it is a way to extend snorkeling and recreational diving to a 20-meter depth range for about an hour without the need for scuba tanks, high pressure oxygen tanks, breathing gas compressors, or other dive-related support equipment or services. Again, while the current disclosure presents the current design of the Pneuma Lung apparatus, it will be appreciated that the Lung incorporates numerous individual inventions and inventive concepts in which patent protection is sought, and it is not necessary to practice the Lung as disclosed herein to take advantage of one or more of such inventive concepts.

This exemplary embodiment of this disclosure (Lung) is part of a four part system that includes a smartphone or tablet mobile device (Smartphone) with a unique Pneuma application (App), the Pneuma Augmented Reality Mask (Mask), and the suite of Pneuma internet-based cloud services (Services).

The Lung is self-instructing using virtual and augmented reality software in the App, augmented reality software in the Mask, and advanced sensors and software in the Mask and Lung. Connectivity with the cloud Services connects the user with programed learning, community, and programed reinforcement of skills, destination information, travel services, games, content creation, and content posting and viewing.

The Lung is made ready to use with three user field replaceable units (FRU) that recharge the device. Each FRU is recycled or disposed of after use. The novel use of replaceable recharge units is an advantage as they (1) simplify device assembly to the insertion of three components, (2) assure the use of renewed critical components, (3) eliminate the need for O-ring seal or device maintenance, (4) eliminate the need for external services and scuba compressors, (5) eliminate the need for biological disinfecting, (6) eliminate the need for oxygen certifications or permits, and (7) eliminate the loss or breakage of disassembled parts.

Each FRU has an energy-harvesting radio frequency RFID memory device (Tag) embedded in the FRU to assure the correct FRU is used and to assure the FRU is installed correctly. Each Tag has a central processor, memory, power management, and cryptographic security. The Tags are energy harvesting, thus needing no battery or other maintenance. The Tags collect radio-magnetic energy wirelessly for their internal power supply and need no mechanical connections. Alternate embodiments of the Tags may use batteries or may be charged by electrical or inductive coupling to another power source.

The Lung is made ready to use by (1) attaching a single hose FRU to a mating conformal-seal connecting receptacle, (2) placing a carbon dioxide scrubber FRU onto a magnetic latch, and (3) attaching a low pressure oxygen cartridge FRU into a seal-free thread fitting.

Correct installation of each FRU is sensed by the electronics and acknowledged back to the user with the Smartphone App.

If the Lung battery needs to be charged, this is done wirelessly with same Qi wireless charger used for the Mask and most Smartphones.

On the surface, and prior to a dive, the primary user interface is the Smartphone and App. User identification, assembly, make-ready and validation, and system configuration are all done with the Smartphone and App.

In the water, the information display for the Lung is provided by the augmented reality display in the Mask. The Lung is fully automated and has no need or provision for user adjustments in the water. Among other data, the Lung provides an integrated time-to-go value to the Mask, which combines all dive time limiting parameters into a single time-to-go value.

The Mask has a unique underwater navigation system to guide the user to destinations, points of interest, and exit points, creating its own local knowledge guide. The Mask navigation system visually guides the user in three dimensions to desired locations and records the users path in three dimensions for later upload. The Mask is more fully described in U.S. patent application Ser. No. 16/406,778, the disclosure of which is incorporated herein by reference.

After activity, the Lung uploads the dive log to the App and then to the Services when an internet connection becomes available. The self-teaching software in the App is able to make recommendations from the dive log data to improve skills and challenge the user to pursue advanced skills.

The Lung fluidically and electronically connects to the Mask using a novel co-axial, bi-directional breathing hose assembly FRU and a short range electromagnetic digital link. Advantages over prior art apparatuses include the Lung hose FRU, which is a single co-axial hose, contains new one-way valves, and has a unique polymer conformal mating surface which needs no maintenance. The entire hose FRU is attached to the Lung with a single keyed twist lock connector.

Counter-lungs are fluid tight flexible containers that hold the approximate capacity of the users exhaled breath in counter to the user's own lungs. The novel inhale and exhale counter-lung design of the present disclosure is a single atomic unit combining both containers into a single vessel. An advantage over the prior art is a novel water trap, and a volume of hydrogel in the exhale counter-lung absorbs liquids that may enter the breathing loop. This traps and contains liquid that may enter the system, preventing excessive liquid contamination of the breathing loop and sensors.

Another advantage over the prior art the co-axial breathing hose is that the water trap and the counter-lungs are a singular FRU that may be recycled or disposed of after use. As such, they do not need to be cleaned of the bacterial and/or viral residue collected by use. The embedded Tag in each hose FRU provide a unique ID for each FRU that is used to track the unit and help assure that it is not improperly reused or incorrectly installed.

The hose FRU is mechanically and fluidically connected to the carbon dioxide scrubber housing with a novel fluid-tight twist locking connector. A unique divergent/convergent diffuser between the hose FRU and the scrubber housing directs and conditions the exhale and inhale gas to each side of the novel bi-directional, two-port scrubber cartridge. One side of the cartridge is for the exhale gas, and the other side of the cartridge is for the inhale gas. This diffuser is an advantage over other prior art, as the design assists in even gas pressure across the face of the scrubber cartridge and assists in the flow of gas through the scrubber.

A novel improvement over the prior art is that a differential pressure sensor measures the difference in gas pressure between the exhale and inhale ports at the diffuser. This pressure differential is used by the software to detect and measure parameters of the user's breathing cycle. This information is then used by the software to assist the user's skill development, calculate gas flow and scrubber usage, and warn the user if a risk of over-breathing the scrubber if not corrected in a timely manner.

The scrubber cartridge FRU is novel and has multiple advantages over prior art designs. The cartridge encases and protects the scrubber chemical, which has a pre-engineered deterministic gas flow. The single cartridge is dual-port and bi-directional, scrubbing the breathing gas twice on each breathing cycle. The cartridge has a Tag memory to record and store its own production, testing, and usage data. The cartridge is fail-safe to install and in operation. A spent scrubber is detected and will not be validated. The prior art scrubbers use granular material or spirals of raw open material, which must be skillfully packed into a canister, the correct compression applied to the material, be properly assembled into a canister, and sealed with O-rings. In the prior art, some scrubber material has a dye to indicate carbon dioxide absorption. The dye is not permanent and will fade back to the natural color of the material over time. In the prior art, extensive training and careful practices are mandated to prevent prior use of spent scrubber material from accidentally being reused. The Tag memory of the present invention prevents any spent scrubber FRU from ever being reused. As shown in the diagrams, a security cryptography in the Tag memory prevents unauthorized attempts to modify the data in the Tag or attempts to bypass this fail-safe feature.

The chemicals that make the active component of the carbon dioxide scrubber FRU are ground, mixed with a polymer binder, and preformed into engineered air flow channels. The scrubber material is then encased inside a cartridge, which protects the material, directs gas flow through the channels in an orderly and deterministic manner and prevents modification or misuse of the material.

Each scrubber cartridge has an embedded Tag to record and track cartridge production, insertion, validation, gas flow, and usage. This information is also used to help prevent reuse of a spent cartridge, as the Lung will not validate with a spent scrubber cartridge.

The opposite side of the scrubber housing is fluid connected to the mixing chamber, which measures the exhaled breath for oxygen content, pressure, and temperature. An absolute pressure sensor, oxygen partial pressure sensor, temperature sensor, electronic oxygen injector valve, and automatic diluant valve are located in the mixing chamber.

The oxygen partial pressure, absolute pressure, and temperature sensors are used by the software and algorithms to determine if the oxygen partial pressure is too high, too low, or in the correct range for the current depth and mode of operation.

An electronic valve in the mixing chamber may meter oxygen into the chamber based on the oxygen partial pressure target set by the software. Using a novel design, the oxygen is injected into a well, which also contains the oxygen sensor. When oxygen is injected, the sensor detects an increase in the oxygen partial pressure, confirming to the software that oxygen is being injected into the breathing loop.

An improvement of the device disclosed in U.S. patent application Ser. No. 16/409,253 (the disclosure of which is incorporated herein by reference) is that a novel mechanical shutter is positioned near the injector well in a manner that allows the shutter to partially enclose the well and the oxygen sensor, obstructing the breathing gas from the face of the oxygen sensor. When the shutter is moved to the closed position and oxygen is injected into the well, the sensor will detect an increase in oxygen partial pressure as the breathing gas is purged out of the well. An advantage over prior art designs is that the shutter, in conjunction with the absolute pressure and temperature sensors, may be used to test and/or calibrate the oxygen sensor and/or the oxygen injector valve at nearly anytime, including during the dive.

A novel element of the present disclosure places a pressure demand valve in the mixing chamber. This valve opens to inject dilution gas into the breathing loop if the pressure in the loop falls below a pre-set delta of the ambient pressure. This valve is able to increase the volume of gas in the loop due to compression of breathing gas during descent, gas lost due to leakage, or gas vented during the ejection of water (and some gas) from the Mask. An improvement over the prior art is that placing the valve in the mixing chamber eliminates the failure points of hoses and user connections between the diluant gas source and the valve.

Novel to the design is that a low-pressure oxygen cartridge FRU is threaded into an automatic valve and pressure regulator. The threaded portion of the cartridge has no seals to maintain or be damaged. The automatic valve opens the cartridge when inserted and closes the cartridge when removed, as such no valve is required. A single stage balanced pressure regulator reduces the gas pressure and is fluid connected to the oxygen injector valve. A novel design feature and an improvement over prior art is that the ambient counter-pressure to the regulator is fluid coupled to the mixing chamber, thereby preventing water ingress or contamination to the regulator and proving a precise pressure drop across the oxygen valve orifice. A pressure sensor is fluid connected to the automatic valve to measure the gas pressure inside the cartridge. The cartridge FRU has a Tag to track the installation of the cartridge, cartridge production data and its use.

A novel flexible pressure bladder is fluidly connected to a single stage demand valve, which is further fluidly connected to the mixing chamber. A pressure sensor is fluidly connected to the high side of the demand valve to measure the pressure inside the bladder. A quick type gas-fill connector is fluidly coupled to the bladder to enable a portable hand or low-power electric air pump to refill the bladder without removing the bladder from the Lung. This flexible bladder is an advantage over prior art systems, as the deflated bladder is safe to transport and is refilled by the user with a hand pump.

A novel removable electronics pod attached to the mixing chamber contains all the control electronics, battery, oxygen sensor, oxygen valve, pressure sensors, RF electronics, and wireless charging circuits. If the Lung were to need service, a single plug-in pod is exchanged to refresh all electronics, battery, and sensors. An advantage over the prior art is that all failure prone interconnect wires and connectors to critical components are eliminated.

The mixing chamber is fluid connected to the novel second port of the bi-directional scrubber FRU, which provides additional and redundant scrubber material to further remove any carbon dioxide from the breathing gas prior to the inhale counter-lung.

A novel design is that using a snorkel with a pressure sensing valve connected to both the inhale and exhale ports of the Mask provides ambient pressure surface-supplied air to the oronasal cup when the Mask is on the surface and a pressure release valve to the breathing loop during underwater use. The pressure differential between the ambient surface air at the top of the snorkel and the water pressure on the submerged outer surface of the flexible counter-lungs directs gas flow to and from the snorkel when the Mask is on the water surface. When submerged, the pressure valve closes, preventing air or water from the ports of the snorkel. When this valve is closed, pressure differential directs exhale gas from the oronasal cup to the co-axial hose and through the unit to be conditioned and re-inhaled.

When the Lung is ascending up the water column from a depth gas inside, the breathing loop is expanding in volume due to the reduced water pressure. This expanding gas may exceed the tidal volume of the two counter-lungs and the users lungs. The increased gas volume increases the pressure inside the closed breathing loop. When the differential pressure between the loop and ambient exceeds the differential cracking pressure of the valve at the top of the snorkel, excess gas is vented through the snorkel valve controlling the gas pressure in the breathing loop.

Various aspects of this invention will become apparent to those skilled in the art from the following detailed description of the preferred embodiments, when read in light of the accompanying drawings.

BRIEF DESCRIPTION OF THE DRAWINGS

FIG. 3 is a diagram showing the Hose FRU.

FIG. 4 is a diagram showing the hose to Mask coupler and one-way valve.

FIG. 29 is a schematic diagram of the NFC Tag circuit.

DETAILED DESCRIPTION OF THE PREFERRED EMBODIMENTS

This exemplary embodiment of this disclosure (Lung) is part of a four part system which includes a smartphone or tablet mobile device (Smartphone) with a unique Pneuma application (App), the Pneuma Augmented Reality Mask (Mask), and the suite of Pneuma internet based cloud services (Services).

Figure 1:
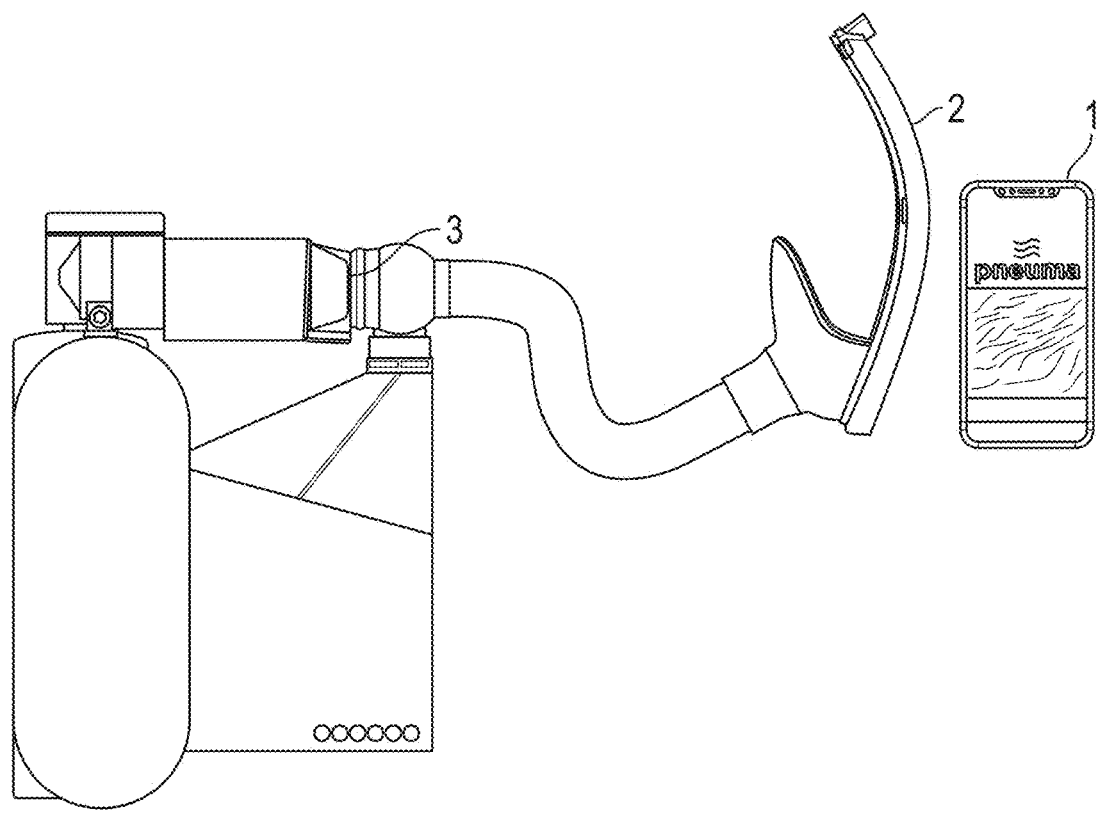
FIG. 1 is a diagram showing the four components of the exemplary system.

The diagram in FIG. 1 lists the current functions and how they are distributed between the four parts of the system. The functions listed and/or the distribution of the functions are not intended to be limiting. They show the current state of the system and a method of distributing functions across multiple devices.

Figure 2:
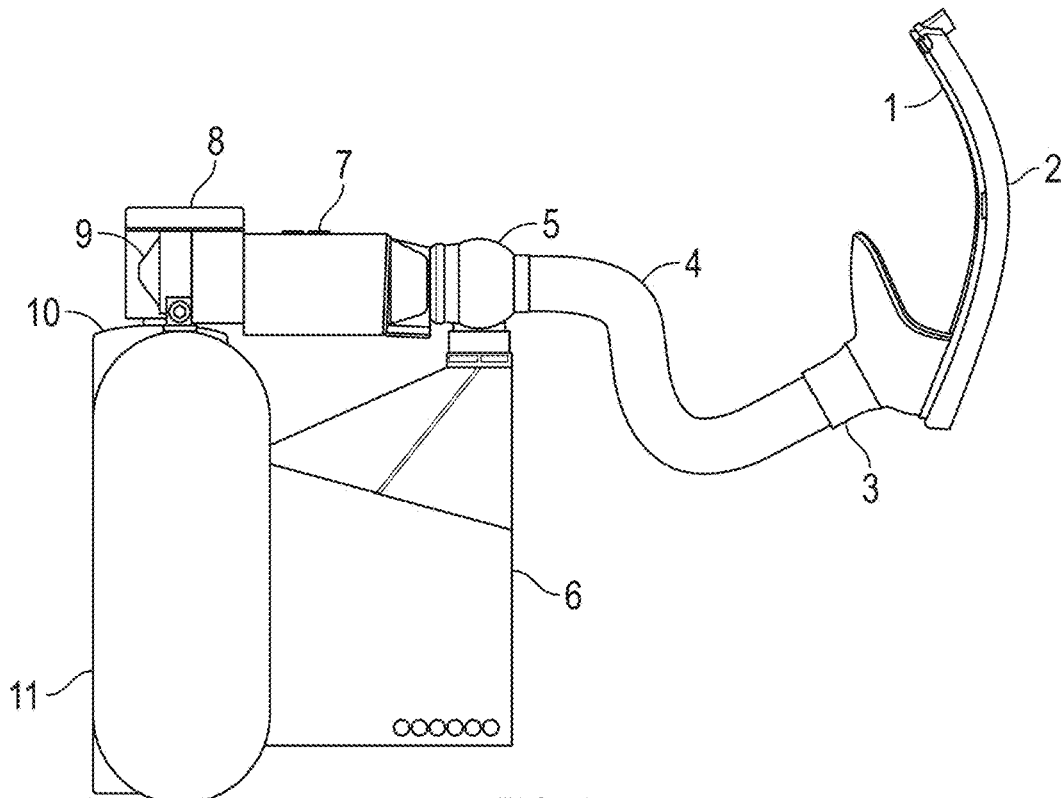
FIG. 2 is a diagram showing the eleven major parts of the exemplary system.

The diagram in FIG. 2 shows the novel relationships and communication links of the disclosed invention between the App, the Mask, the Lung, and the Services. The Smartphone contains the wide area networking, cellular, and WiFi services through the App. The Smartphone and App connects the Mask and the Lung to the cloud Services. The App reads the QR code seals on the FRU packages using the Smartphone internal camera and reads and writes data to the Tag of the three FRU's using the internal Near Field Communications (NFC) radio of the Smartphone. The NFC radio in the Smartphone may also read the user ID from one or more other Pneuma Masks to enable the Pneuma-to-Pneuma data link for the LiFi optical data communications. The Smartphone establishes data connections, such as Bluetooth connections, with both the Lung and the Mask, while the Lung and the Mask also establish a Bluetooth data connection between each other. The Mask creates optical LiFi links to other Masks. The Lung creates NFC links to the Tag of the FRU components of the Lung and periodically updates data in the Tags during use.

FIG. 1 shows the assembly and location of components in the current embodiment of the system with the Smartphone 1, the Mask 2, and the Lung 3 without the Lung frame, cover, and attachments.

Figure 26:
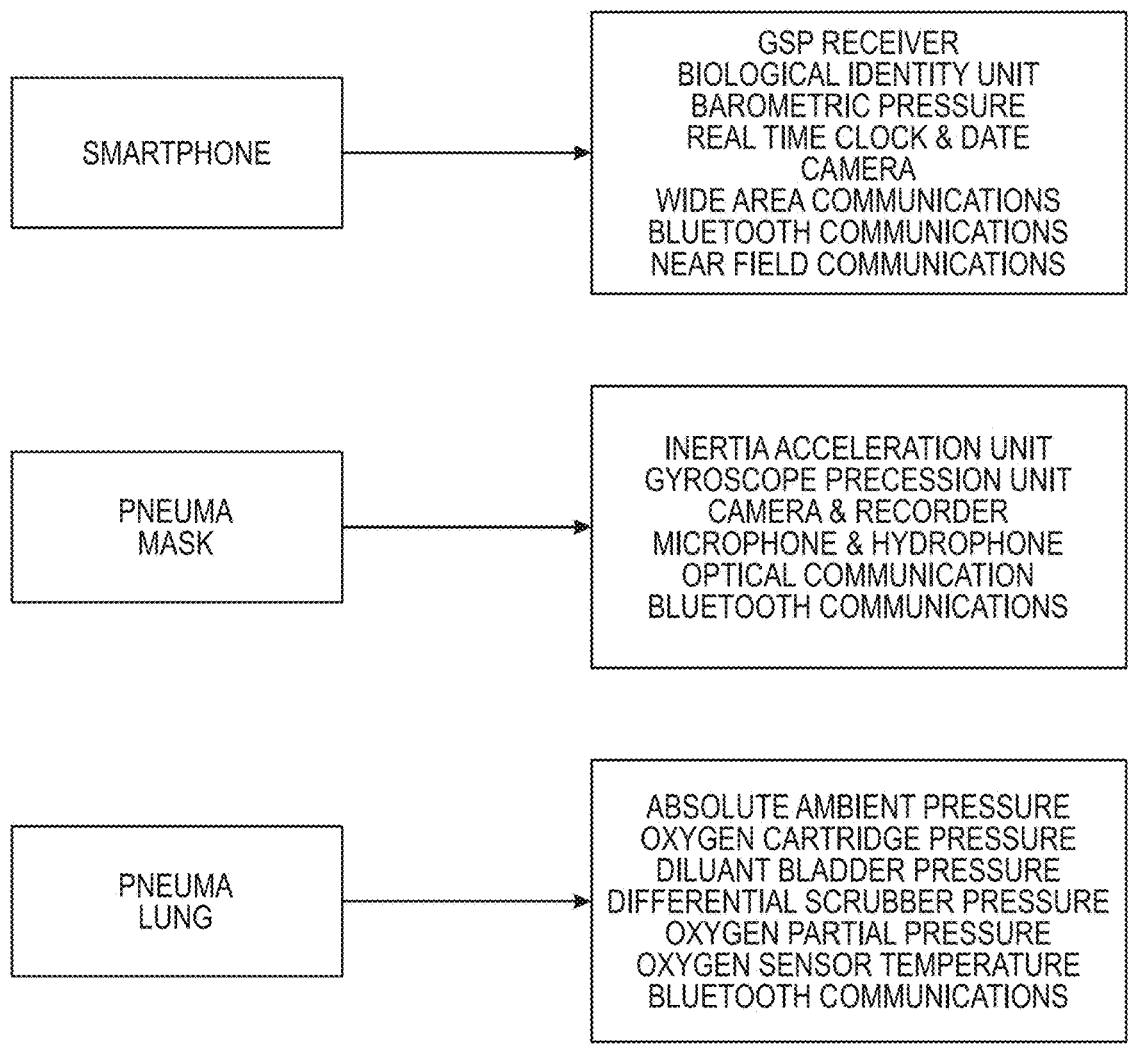
FIG. 26 is a flowchart of the distributed sensors of the Pneuma system.
Figure 27:
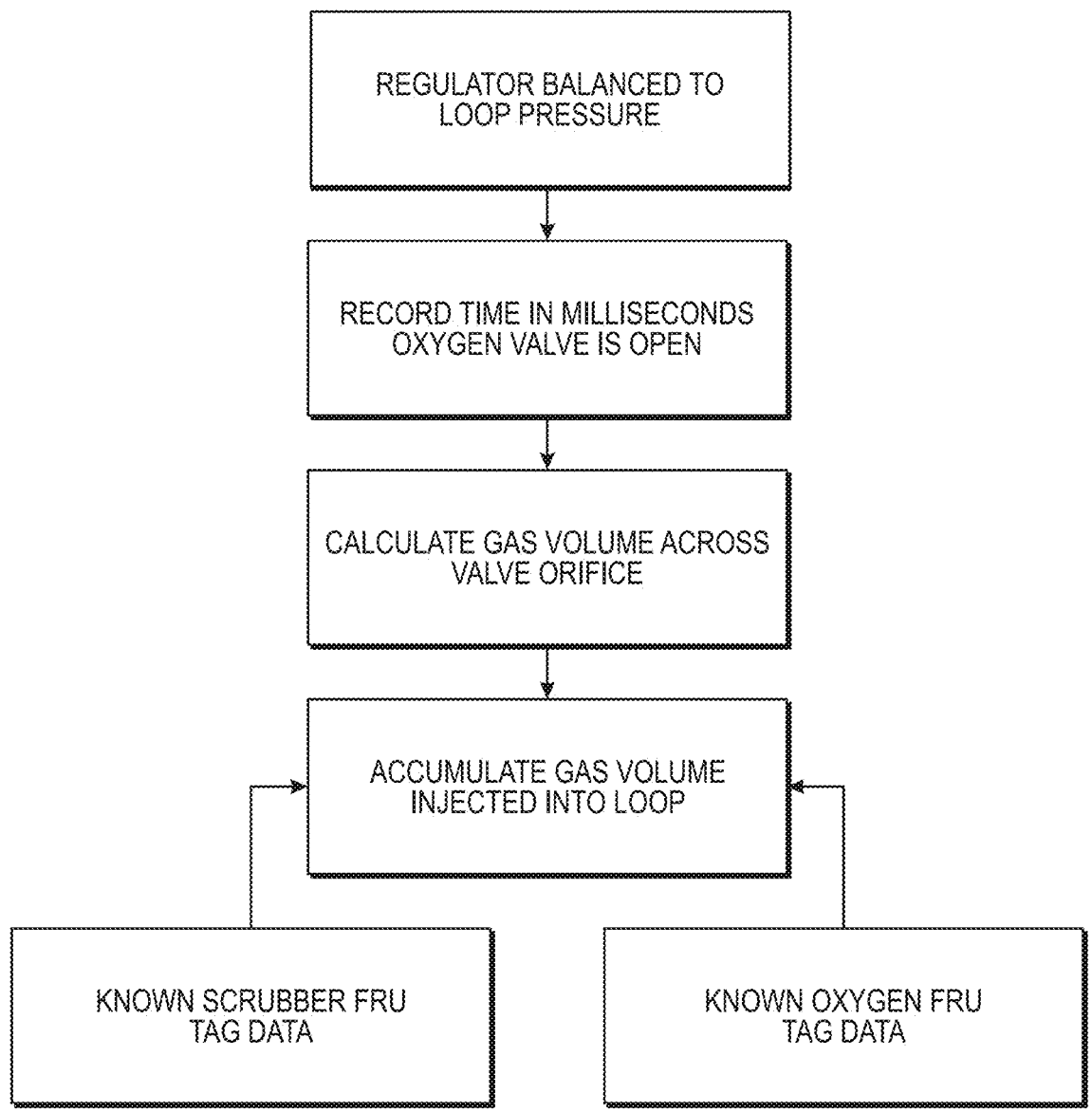
FIG. 27 is a flowchart of the oxygen volume calculation.

The Lung is a self-teaching and fail-safe design using a novel distributed methodology for software, processors, and sensors. The processes and sensors required are distributed between the Smartphone, the Mask, and the Lung as shown, for example, in FIG. 26. The description, function, and implementation of the sensors is covered in the appropriate detail sections to follow.

FIG. 2 shows the assembly, location, and major components of the current embodiment of the Lung.

The Mask, with an augmented reality display and electronics are described in more detail in above-referenced U.S. patent application Ser. No. 16/406,778.

The design avoids many of the complications and negative effects of the prior disclosed apparatuses and methods of the prior art and is designed to be self-training and fail-safe.

An improvement over the prior art the device is designed for self-training, which is detailed later in this disclosure. Self-training is accomplished, among other things, by using the Services-based training software in the App, the augmented reality digital recognition of components and their assembly in the App and Mask software, the make ready assembly of the unit with three pre-tested units, the RF Tag in each FRU to uniquely identify and detect proper assembly of the device, and the sensors in the device to monitor proper operation and use and the apparatus.

The device of this disclosure is considered fail-safe as it will not transition to a Ready status unless it is validated prior to use, and then gives the user more than 2.5 times the industry standard recommend time to surface after detecting a malfunction. Reading the Tag memory of the three pretested recharge FRU twice, once in the App and again in the Lung, the device software knows the detail data of each recharge unit and receives a positive indication when each FRU is installed correctly. Reading the oxygen and diluant pressures assures adequate volumes of gas are present. The software tests and validates the oxygen injector valve using power measurements and confirming gas flow. The software tests and calibrates the ambient pressure sensor using the redundant sensor in the Smartphone to validate and/or calibrate the sensor in the electronics pod. The system tests, validates, and calibrates the oxygen sensor using the calibration shutter and the oxygen injector valve. The $O_2$ canister contains a known gas from manufacturing and is not refillable and thus, does not need to be tested by the user prior to use. The designed gas $PPO_2$ limits will get the user back to the surface with an open or closed state failure of any valve and/or an electrical failure. Once on the surface, the unit automatically switches to surface air.

The Mask is attached to the Lung mechanically, electronically, and fluidly using the disposable hose FRU shown in location in FIG. 2 (3,4,5) and a short range radio link. The present embodiment implements a 2.4 GHz radio and the Bluetooth protocol stack with one radio located in the Mask display unit 2 and a second radio located in the electronics pod shown in 8. An improvement over the prior art, the Lung uses redundant packet radio communications to the user interface rather than cables and connectors, which may fail in corrosive salt water.

A novel element of the invention is the disposable hose FRU shown complete in FIG. 3. Each hose FRU assembly is made of typically seven components factory joined together as a single unit, as shown in the diagram in FIG. 3 at 1-7. One of the many advantages of using disposable components for the portions of the breathing loop in contact with human fluids is the elimination of the need for biological cleaning of the Lung after use. This also eliminates the need to instruct the user on the need and proper techniques of bacterial and viral disinfecting. Another novel element of the current disclosure is the placement of the two one-way valves in the breathing loop with the hose FRU. This eliminates the potential for damaged or failed valves and eliminates the potential for a valve being damaged or mis-positioned during cleaning. Typical in the prior art, three user-serviced O-rings are needed for the mouth piece valve (DSV), two more O-rings for the exhale to counter-lung hose, two more O-rings for the counter-lung to scrubber hose, two more O-rings for the inhale scrubber to counter-lung hose, and two more O-rings for the inhale counter-lung to DSV hose, for a total of eleven user-serviced O-rings just in the hose assembly. The present embodiment has none.

FIG. 3 shows the location of the oronasal coupler. The hose FRU oronasal coupler attaches to the Mask oronasal cap, making a fluid tight seal to the silicone Mask oronasal seal. The coupler has two circumferential co-axial ports, as shown in FIG. 4. The inner port shown at 2 in FIG. 4 used for the inhalation gas and is covered at the coupler with a one-way silicone mushroom valve 1. The outer port 3 is used for the exhalation gas. The inhalation port has a mushroom valve at the coupler to prevent exhalation gas from flowing into the inhalation circuit and to prevent liquid from entering the inhalation hose. It is preferred the sectional area of the two ports be similar. An improvement over the prior art the mushroom one-way valve is replaced with each new FRU assuring a new undamaged valve is in place.

FIG. 2 shows the location of the co-axial hose at 4. The present embodiment uses medical grade 31 mm convoluted vinyl free hose from Cardinal Health, yet other hoses could be used. It is preferred that the cross sectional area of the inner tube and the space between the inner hose and outer hose be similar as shown at 1 and 2 in FIG. 5. One end of the outer hose 1 is attached to the oronasal coupler at 3. The inner hose 2 of the same end is attached to the oronasal coupler at 2 in FIG. 4. The other end of the outer hose is attached to the water trap FIG. 6 at 2. The inner hose of the same end is attached into the water trap at 3. An improvement over the prior art the use of single co-axial hose reduces assembly complexity, reduces the number of seals, and is more comfortable for the user as the disposable hose is more flexible and connected to the center line of the head, producing less resistance to head rotation.

Figure 5:
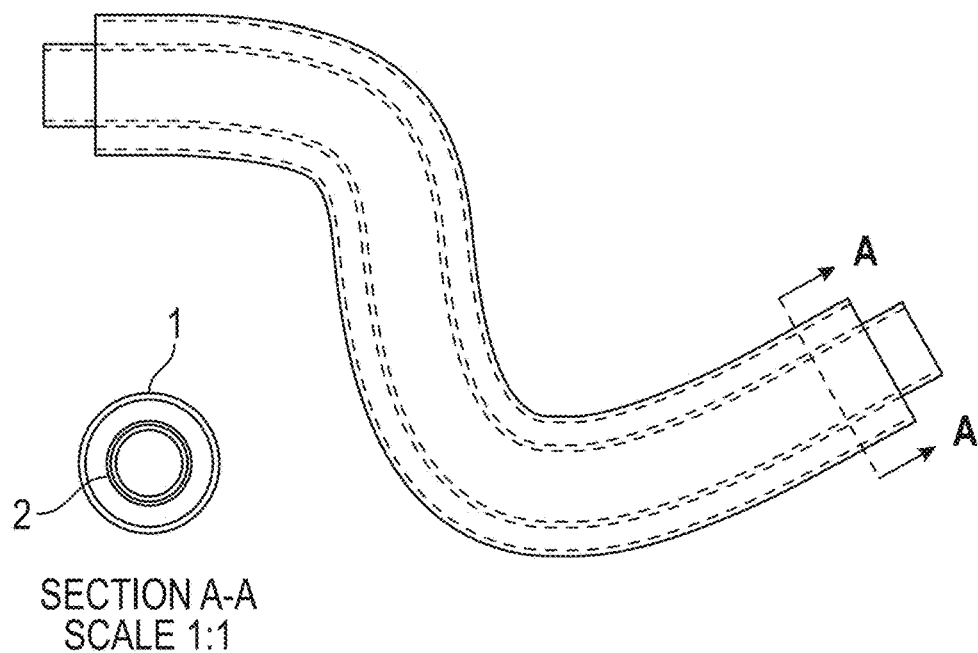
FIG. 5 is a diagram showing the co-axial breathing hose.
Figure 6:
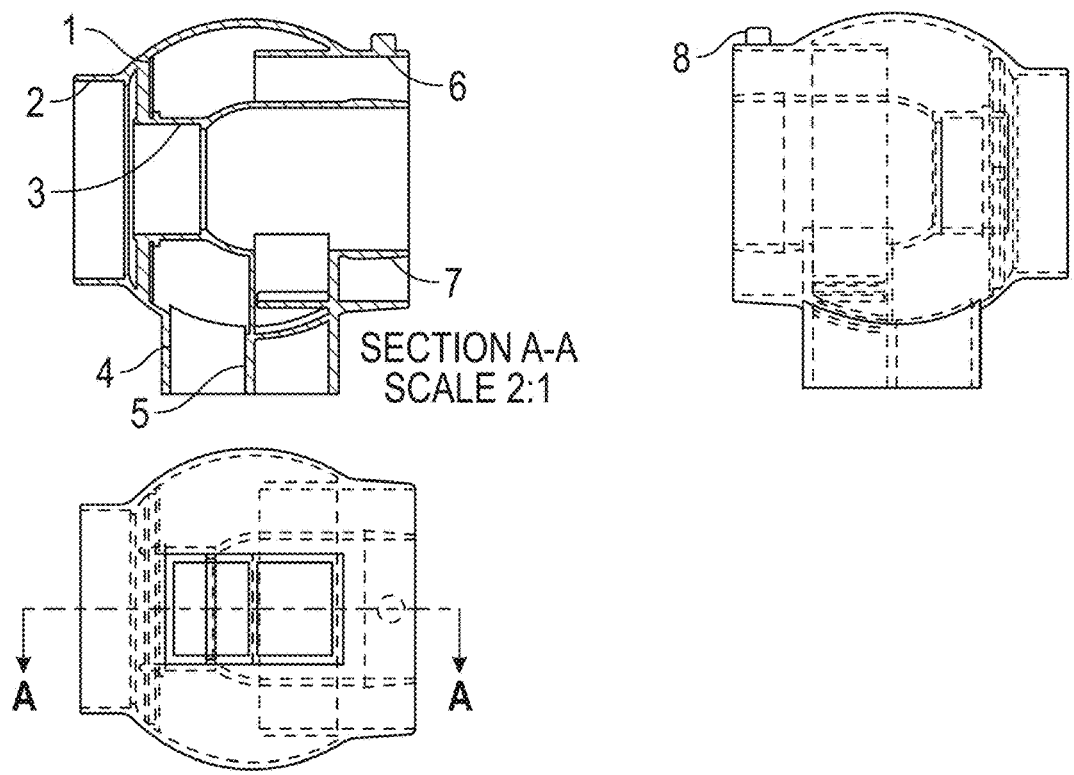
FIG. 6 is a diagram showing the water trap and one-way valve
Figure 7:
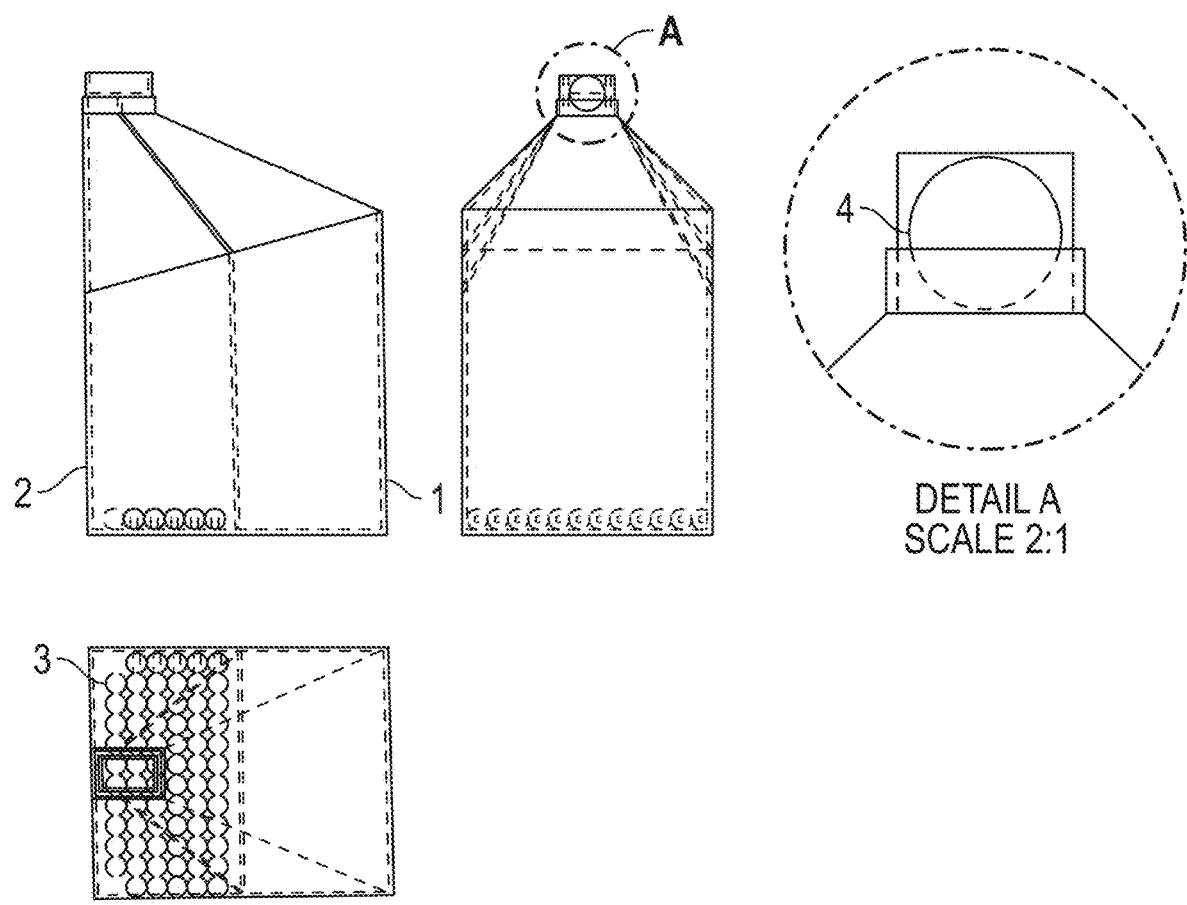
FIG. 7 is a diagram showing the exhale and exhale counter-lungs and the NFC tag.
Figure 8:
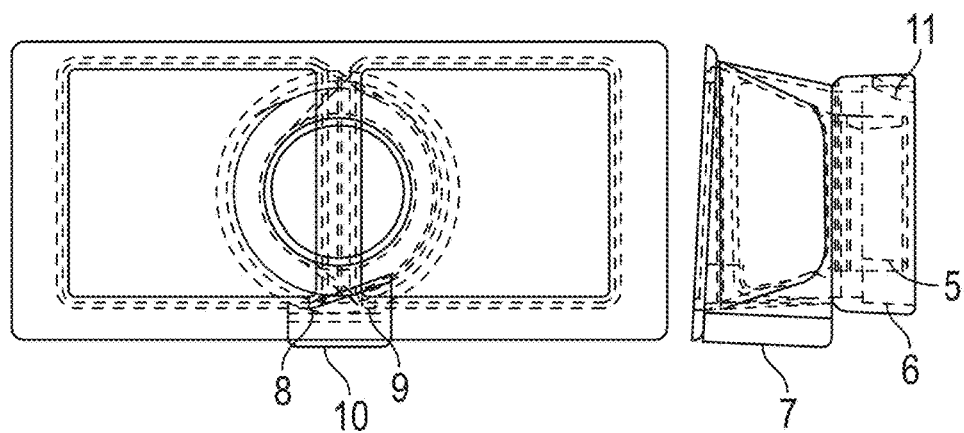
FIG. 8 is a diagram showing the diffuser, pressure sensor, and NFC antenna.

FIG. 5 shows the locations 5 of the novel water trap. In the present embodiment, the co-axial hoses are attached to the flanges 2 and 3 in FIG. 6. The outer port 2 carries the exhalation breath from the user. A silicone one-way valve 1 opens to allow gas flow in one direction during the exhale cycle, while blocking back airflow and liquids from entering the hose during the inhalation cycle. A novel element of the embodiment uses an expanded center section and extended receptor tube to enhance the entrapment of any liquid which may enter the exhalation hose. This liquid is directed to flow through the port shown in FIG. D6(4) and into the exhalation counter-lung shown at 2 in FIG. 7. Inhalation gas flows through the center section of the water trap, as shown in FIG. 6, to the inner hose attached to the flange at 2. A novel element of the current embodiment is the tapered co-axial twist connector to secure the water trap end of the hose FRU to the scrubber diffuser are shown in FIG. 8 at 5 and FIG. 7 at 6. The disposable and conformal tapered flanges of the water trap shown at 6 in FIG. 6 mate to the opposing rigid tapered flange of the diffuser as shown at 6 in FIG. 8. This large taper area seals the port without O-rings or any user-serviced device and aligns the conformal seals on the flanges as shown at 7 in FIG. 6 to the tapper flange 5 of FIG. 8. The protruding pin shown at 8 in FIG. 6 intermeshes with the slot in diffuser flange 11 in FIG. 8 pulling in the water trap and providing compression to the conformal tapper area, as shown 6 and 7 in FIG. 6. Two ports 4 and 5 fluid, connected separately to the exhalation and inhalation path, connect mechanically and fluid to the counter-lungs as shown in FIG. 7. In the prior art, up to eight O-rings are needed to seal the inhale and exhale hoses, while the present embodiment needs none.

Part of the user's exhalation breath is directed through the water trap to the co-axial port at the opposing end of the trap, then through the carbon dioxide scrubber. Some of the breath is temporarily stored in the exhalation counter-lung, as directed by pressures in the breathing loop. Differential pressures between the exhalation counter-lung shown at 2 in FIG. 7 and the inhalation counter-lung as shown at 1 in FIG. 7 motivate gas flow from the exhalation counter-lung through the carbon dioxide scrubber into the inhalation counter-lung during and between exhalation and inhalation cycles. The breathing loop must contain the vital capacity of the user's exhale breath counter to the breathing cycles, this mandates the loop should have a similar or larger vital capacity than the user, the current embodiment is approximately five liters. The current embodiment of the counter-lung uses a novel design of sonic-welded 1.5 mm thick sheets of vinyl with the exhalation and inhalation counter-lung sharing a single center wall, as shown in FIG. 7. The tops of the two counter-lung chambers are sonic-welded to a collar, which also contains a novel energy harvesting RFID Tag as shown at 4 in FIG. 7. This Tag is only visible to the antenna when the hose FRU is in the correct position. This assures the FRU is installed correctly. A unique feature of the disposable FRU design allows a quantity of absorbent polymer hydrogel positioned in the exhalation counter-lung as shown at 3 in FIG. 7 to immobilize any liquid directed to the counter-lung from the water trap. In the present embodiment, colloid beads of saline-resistant polyelectrolyte and ethylene maleic anhydride are used as their ability to absorb higher ion levels. Other forms of hydrogels will also work so long as most of the non-absorbed ions are immobilized in the gel.

The novel carbon dioxide scrubber diffuser as shown in FIG. 8 channels the breathing gas from the exhalation side of the water trap to a 4:1 ratio divergent duct. Using Bernoulli's equations, this slows the gas flow with a corresponding increase in gas pressure through the duct. The slowing of the gas flow and increase in pressure helps to diffuse the gas and even the pressure across the face of the scrubber channels, reducing uneven distribution of gas flow through the scrubber channels. The opposite occurs on the inhalation side of the diffuser. Using a 4:1 ratio convergent duct, the increase in flow rate decreases the gas pressure, helping to pull gas through the inhalation side of the scrubber channels. A novel applications of a differential pressure sensor shown at 10 in FIG. 8 senses the pressure in each side of the diffuser duct using holes in the ducts as respectively shown at 8 and 9 in FIG. 8. This differential sensor is used to detect breath cycles of the user and to calculate gas flow volume through the scrubber material. This is explained in more detail in another sections of this disclosure. A directional 13.56 MHz RF antenna shown at 7 in FIG. 8 reads and writes to the Tag located on the collar of the water trap shown at 4 in FIG. 7. This antenna is highly directional, limiting the ability of the Tag located on the counter-lung to communicate only when the Tag is correctly rotated into position by the water trap pin shown at 8 in FIG. 6.

Figure 9:
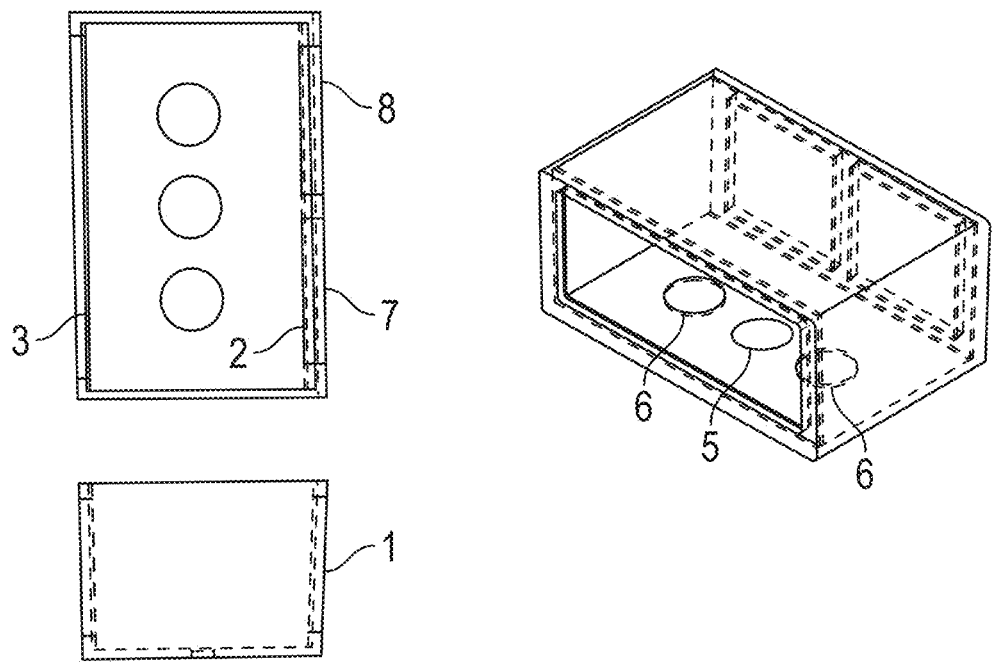
FIG. 9 is a diagram showing the carbon dioxide scrubber housing assembly.

FIG. 2 shows the location of the carbon dioxide scrubber assembly. This novel design uses a FRU scrubber cartridge which is pre-assembled, tested, and contains an embedded Tag to record production, validation, and other data. The scrubber housing shown in FIG. 9 has a novel taper shape, shown in 1, which prevents the scrubber FRU for being installed incorrectly and creates a wedge to set the FRU onto the conformal seals located at each end of the scrubber housing, as shown at 2 and 3 in FIG. 9. The current embodiment housing contains two encapsulated magnets, as shown at 6 in FIG. 9, aligned with matching encapsulated metallic disks in the scrubber FRU as shown at 2 in FIG. 10, The magnets and the matching disks secure the scrubber FRU in the housing and provide the force to maintain the pressure on the conformal seals. While the current embodiment uses magnets to secure the scrubber FRU into the housing, this is not intended to be limiting, and other retention methods may be used. A hole in the bottom of the housing as shown at 5 in FIG. 9 vents any trapped air in the housing and provides a method to push the spent scrubber FRU cartridge from the housing.

The scrubber FRU contains the carbon dioxide scrubber chemical, pre-engineered air flow channels, and the RFID Tag to store and record production, flow and other data. The cartridge as shown in FIG. D10 fits into the housing of FIG. D9 using a matching taper shown at 3 in FIG. 10. This taper prevents the cartridge from being installed in the housing in the wrong orientation and creates lateral pressure between the sealing face of the cartridge and the conformal seal of the housing. In the current embodiment, metallic disks embedded in the cartridge shown at 2 in FIG. 10 secure the cartridge into the housing. An advantage over prior art the cartridge is a singular unit yet design makes two independent scrubber flow paths, one for the exhalation gas and one for the inhalation gas. The scrubber chemical is preformed into engineered channels, as shown at 7 in FIG. 10, parallel with the length of the cartridge. A pointed wedge on the center seal pillar of the cartridge, as shown at 4 in FIG. 10, presses into the chemical block, creating a gas divider between the channels of the exhale side 6 and the inhale side 5. The details of the scrubber cartridge design are further explained in a following section of this disclosure.

Figure 13:
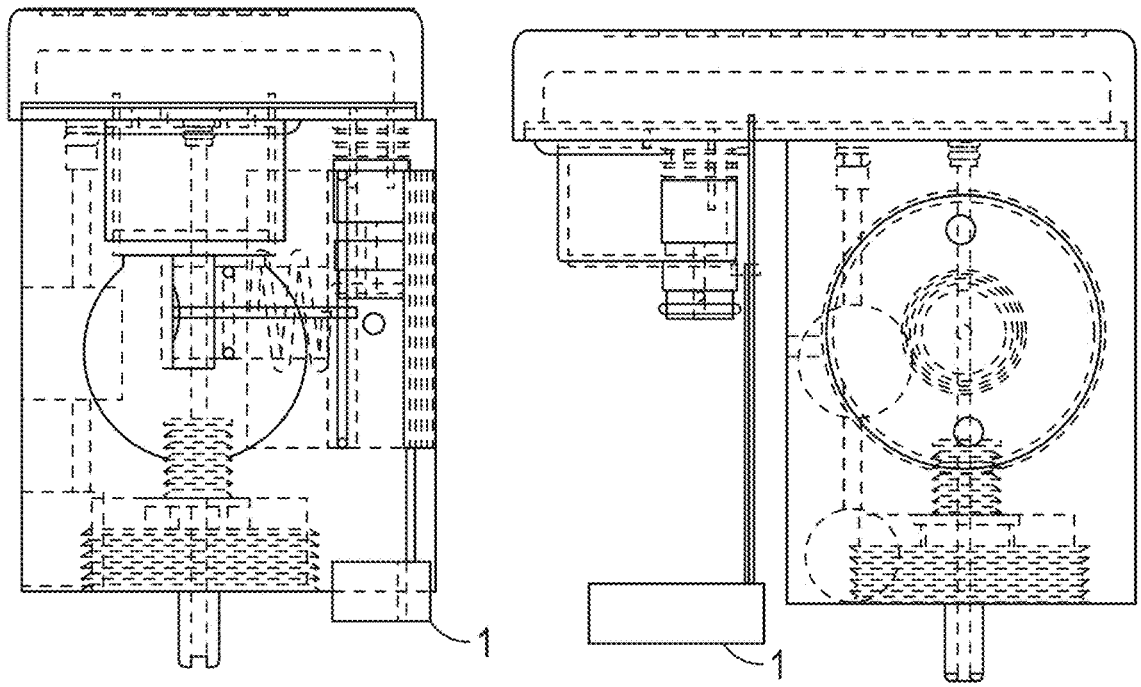
FIG. 13 is a diagram showing the NFC transceiver for the oxygen and scrubber cartridge.

A second 13.5 MHz RF antenna is mounted in the mixer housing as shown at 1 in FIG. 13. This antenna is used to read and write the Tag mounted in the scrubber FRU and the Tag on the oxygen cartridge FRU.

The mixer is located on the back side of the scrubber housing, as shown at 8 in FIG. 2 and contains most of the active devices of the Lung. The mixer receives the exhale gas as it leaves the exhale side of the scrubber. The oxygen sensor shown 1 in FIG. 12 is mounted in the breathing gas flow and measures the partial pressure of oxygen in the breathing gas. More detail on the control of the partial pressure of oxygen is explained later in this disclosure. If oxygen is needed, the oxygen valve shown at 2 in FIG. 12 opens and injects oxygen into the mixing chamber. Absolute pressure sensor 4 measures the pressure in the mixing chamber. If the pressure in the mixing chamber is below the ambient delta threshold value, the diluant valve shown at 9 in FIG. 2 and 7 in FIG. 11 opens and injects diluant gas into the mixing chamber from the diluant bladder shown at 11 in FIG. 2 and mounted to the fitting shown at 9 in FIG. 11. A temperature sensor in the oxygen sensor measures the temperature of the breathing gas in the mixing chamber.

After the mixing chamber, the breathing gas flows through the inhale side of the scrubber FRU, removing any remaining carbon dioxide from the gas and back to the Mask through the hose FRU.

The electronics pod is mounted on the mixing chamber in the location shown at 8 in FIG. 2. This novel design improves on the prior art by having all the electronics, the pressure sensors, rechargeable lithium battery, wireless battery charging, oxygen injector valve, and oxygen sensor mounted on a single printed circuit board and secured into an atomic water tight module. This is an improvement over prior art as connections to critical components including the oxygen sensor, oxygen injector valve, battery, current sensors, and pressure sensors are all on a single printed circuit board without using wires or connectors. Prior art devices have multiple wires and connectors which must be installed and maintained by the user. The cables, wires, and/or connectors may further be exposed to the dive environment including sea water, leading to corrosion and failure during use. Additional improvements over prior art are the use of short range packet RF communications to the user interface and wireless battery charging, eliminating all wires, cables, and connectors which are subject to failure in the water immersion environment. FIG. 12 shows the pod and the major sensors including the oxygen sensor 1, the oxygen injector valve 2, the diluant bladder pressure sensor 3, the mixing chamber pressure sensor 4, oxygen cartridge pressure 5, and the rechargeable lithium-polymer battery 7. The battery is wirelessly charged by placing a Qi compatible wireless charger on the case at the location shown at 6. A novel feature is the ability to renew all the electronics, oxygen valve, oxygen sensor, pressure sensors, and battery with the replacement of a single field replaceable pod. In the current embodiment, the major components of the electronics pod are a Nordic nRF52840, Cortex M4, NXP PN532, Clippard ST3C and multiple TE MS5837 sensors.

Figure 24:
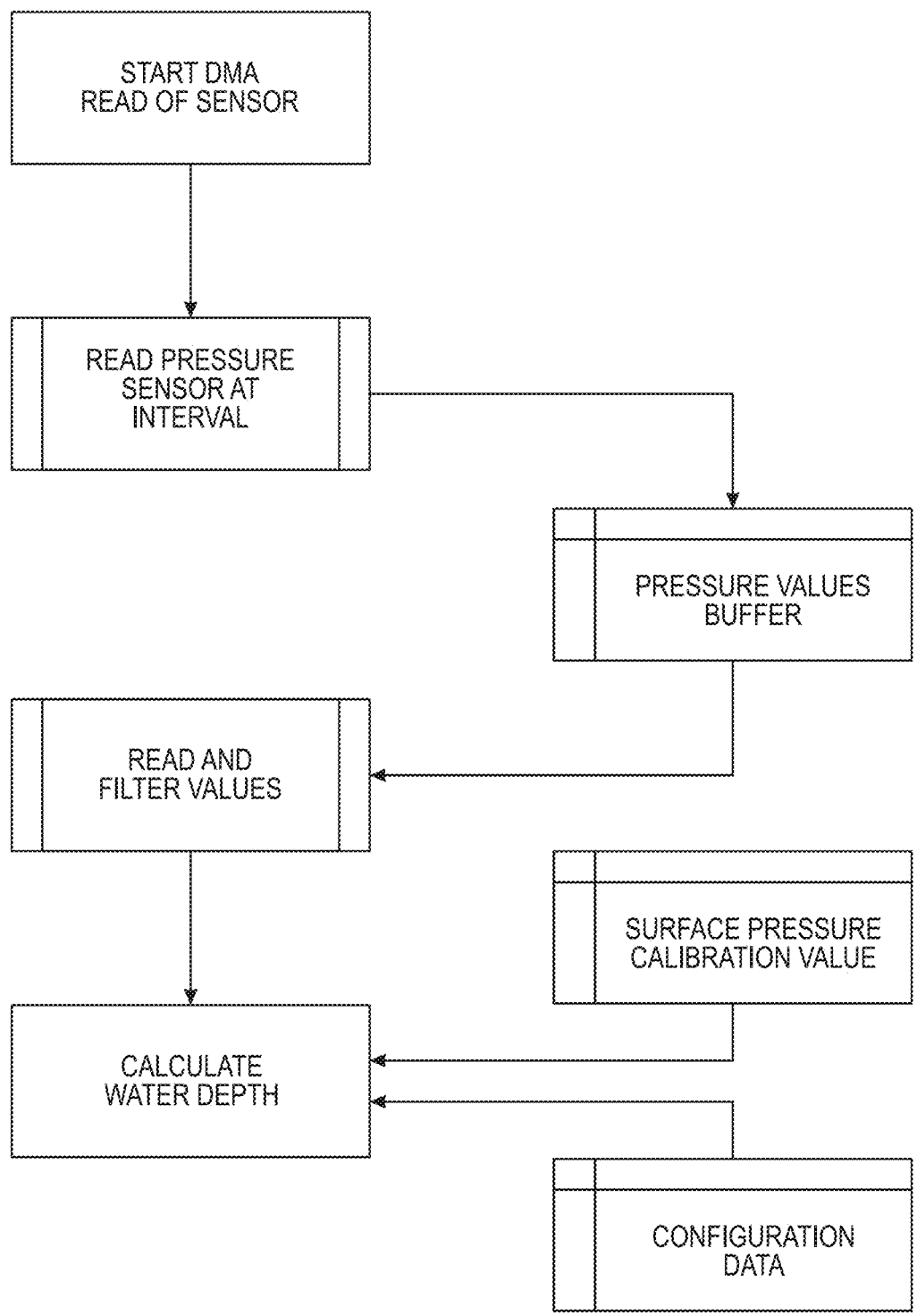
FIG. 24 is a flowchart of the water depth calculation.

Novel in the design and an improvement over prior art is the use of the mixing chamber pressure sensor shown in FIG. 12 to determine dive depth. The combination of counter-lungs 1 and diluant valve 7 in FIG. 11 keep the pressure in the mixing chamber very near the ambient pressure of the surrounding water. In the current embodiment, the pressure sensor is read on a periodic time interval and the value written into a buffer memory using a direct memory access controller. The software filters the values and determines a mean value. This is corrected to the surface pressure as recorded prior to the dive using the sensor and the Smartphone App and the water type setting in the configuration array. This value is then converted to dive depth—see the flowchart in FIG. 24. This method is an advantage over prior art as the pressure sensor is not subject to exposure to the water or contaminants of the dive environment, increasing sensor life and eliminating the need to clean the sensor after use.

An improvement over prior art is the use of a single oxygen sensor as shown at 1 in FIG. 12 on the electronics pod. Prior art systems use more than one oxygen sensor to be able to detect a sensor error. The industry standard of prior art was tertiary sensors with voting logic to identify and isolate a sensor not agreeing with the two others. This method has flaws as double sensor error due to drift are not uncommon, and the voting logic will then remove the good working sensor and lock to the two sensors in error.

Figure 22:
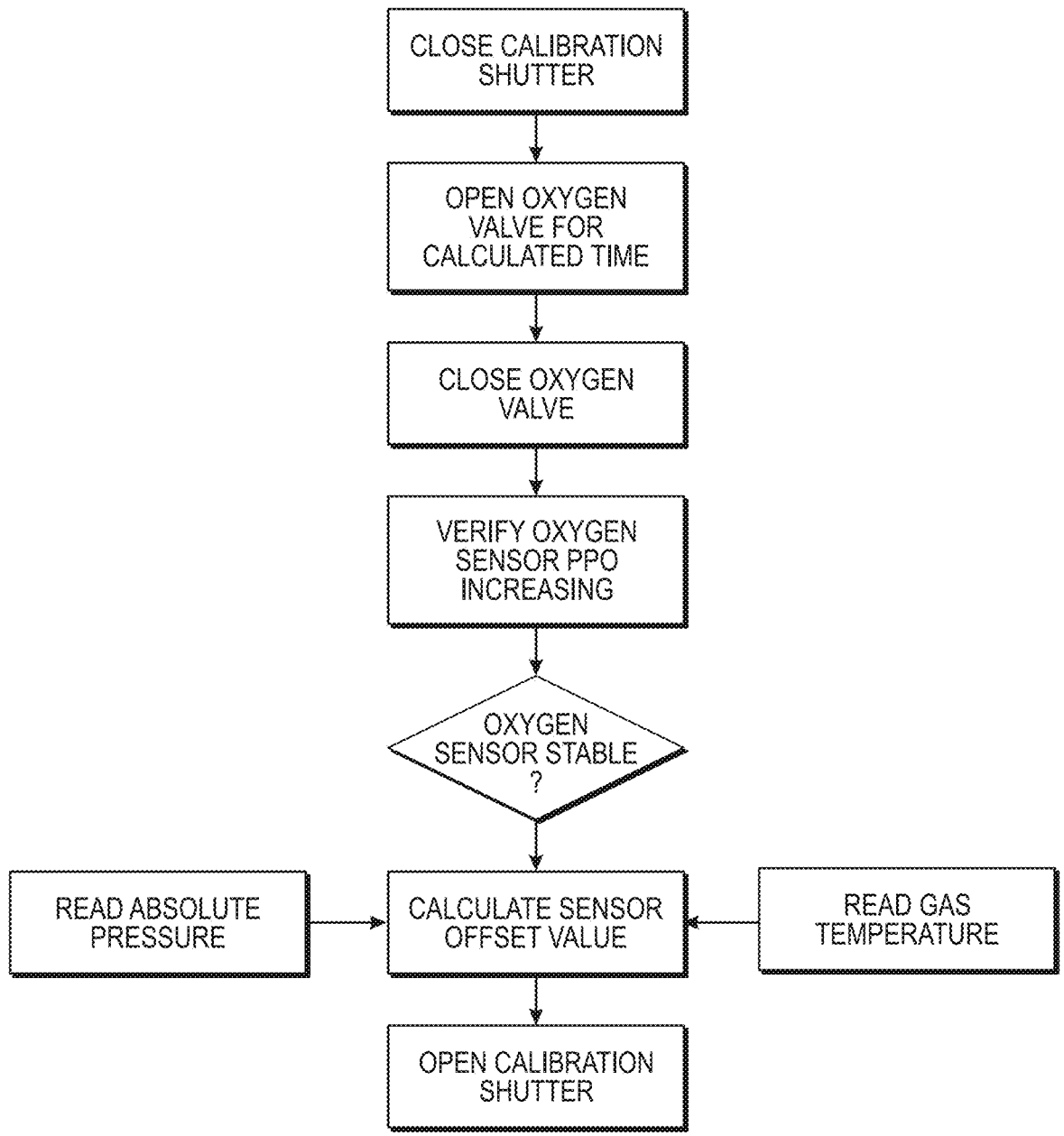
FIG. 22 is a flowchart of the calibration system.

The novel solution used in the current disclosure has a single oxygen sensor using Clark, galvanic, or fluorescent quench technology. The cell is tested and calibrated prior to use and periodically during use to recalibrate the sensor for drift errors and/or detect a failure. This is done by enclosing the sensor in a well with a movable shutter valve. Oxygen is injected into the well while the gas pressure and temperature is measured—see the flowchart in FIG. 22.

Figure 14:
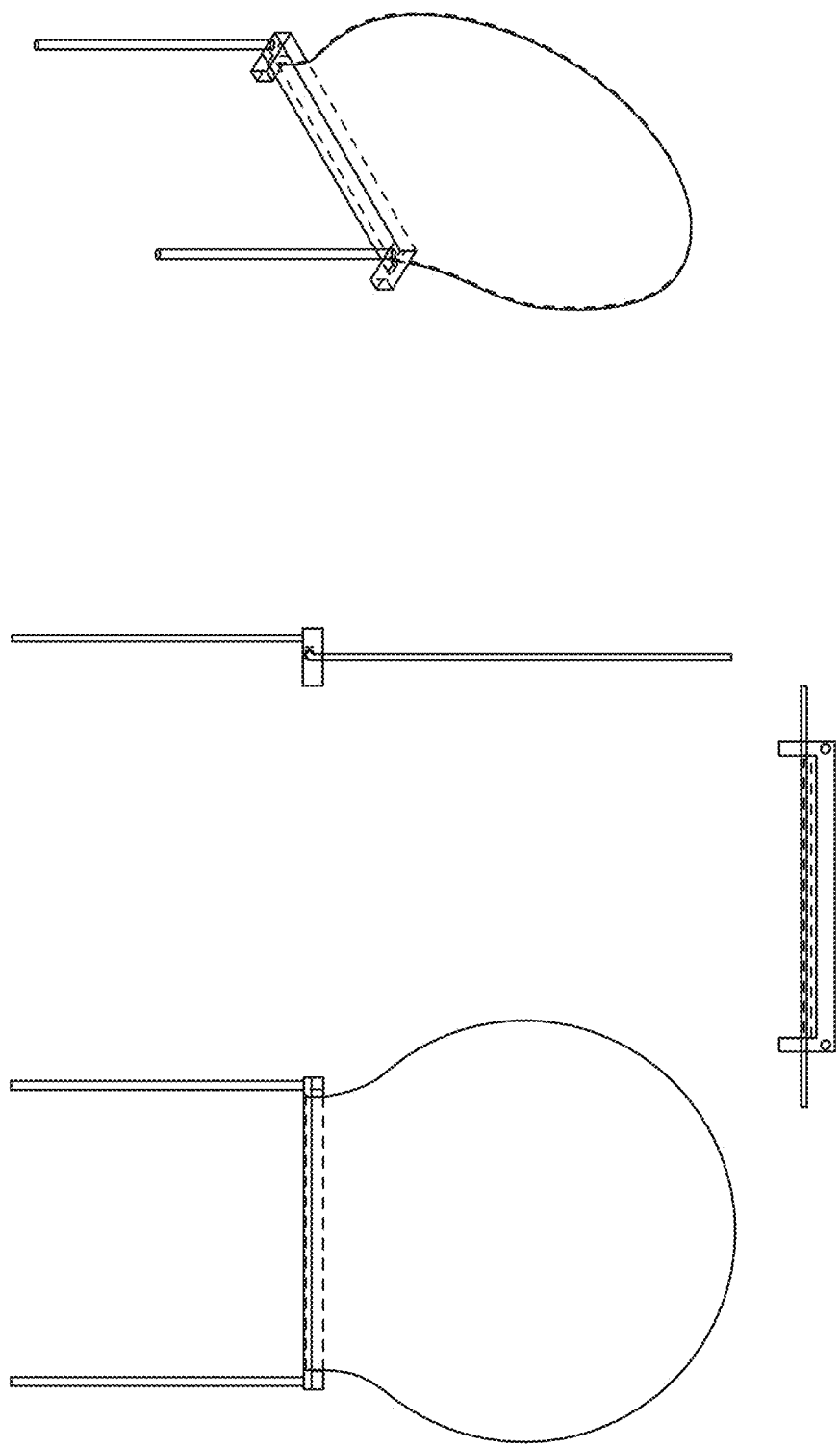
FIG. 14 is a diagram showing the calibration shutter in the operating position.
Figure 15:
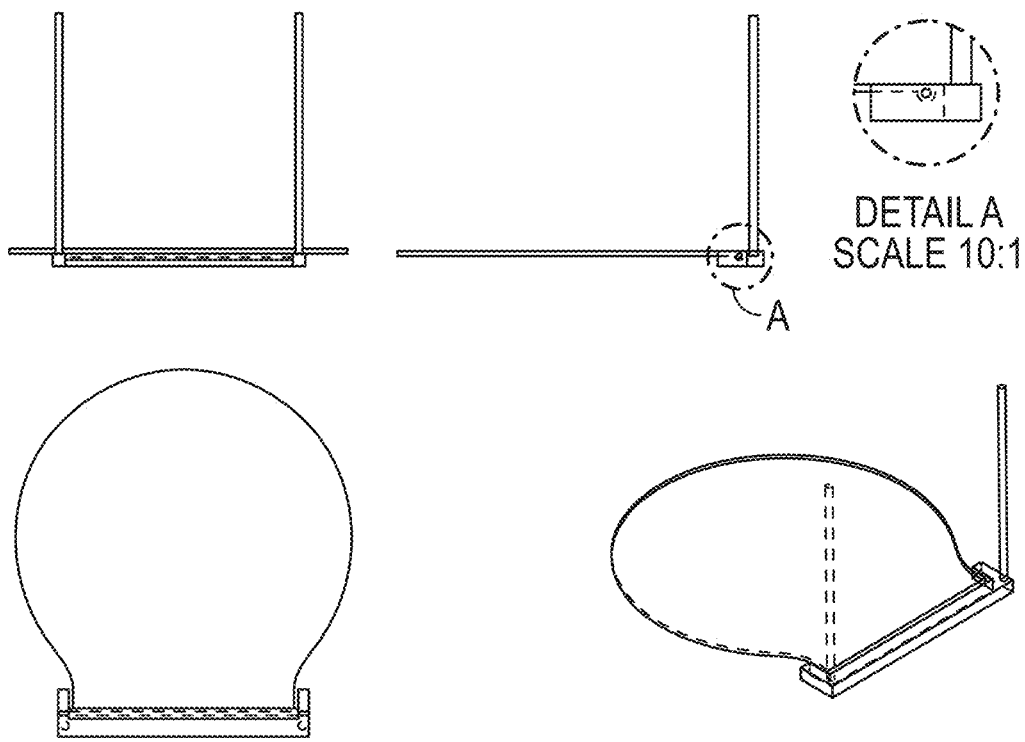
FIG. 15 is a diagram showing the calibration shutter in the calibration position.
Figure 16:
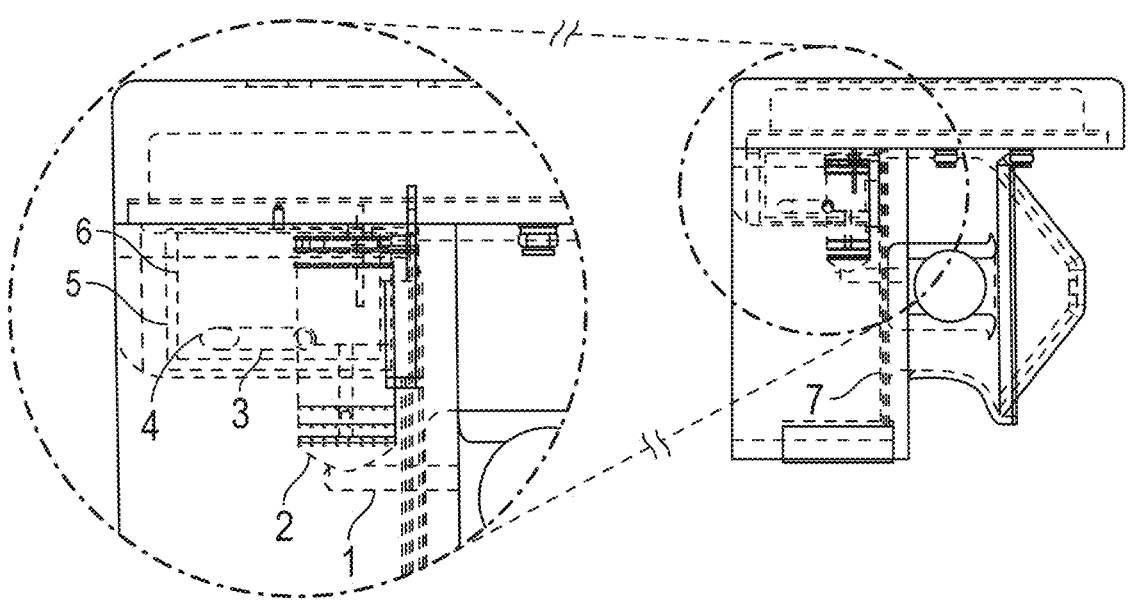
FIG. 16 is a diagram showing the injector valve and oxygen sensor detail.

The oxygen sensor 6 shown in FIG. 16 is located in a well, as shown at 5. The shutter shown at 7 then rotates 90° to cover the well. Oxygen injector valve 2 injects oxygen into the well using the port 3. FIG. 14 shows the shutter detail in the open position. When desired for calibration, the electronics applies a current through the wires 4 and 5 in FIG. 14 on either end of the circuit board 2. The titanium nickel alloy nitinol wire 10 connected across the circuit board heats with conducted current twisting 90°, rotating the attached shutter 5 to the closed position as shown in FIG. 15. After the calibration is achieved, the current to the nitinol wire is removed, and the shutter rotates back to the 0° position as the wire cools.

Figure 10:
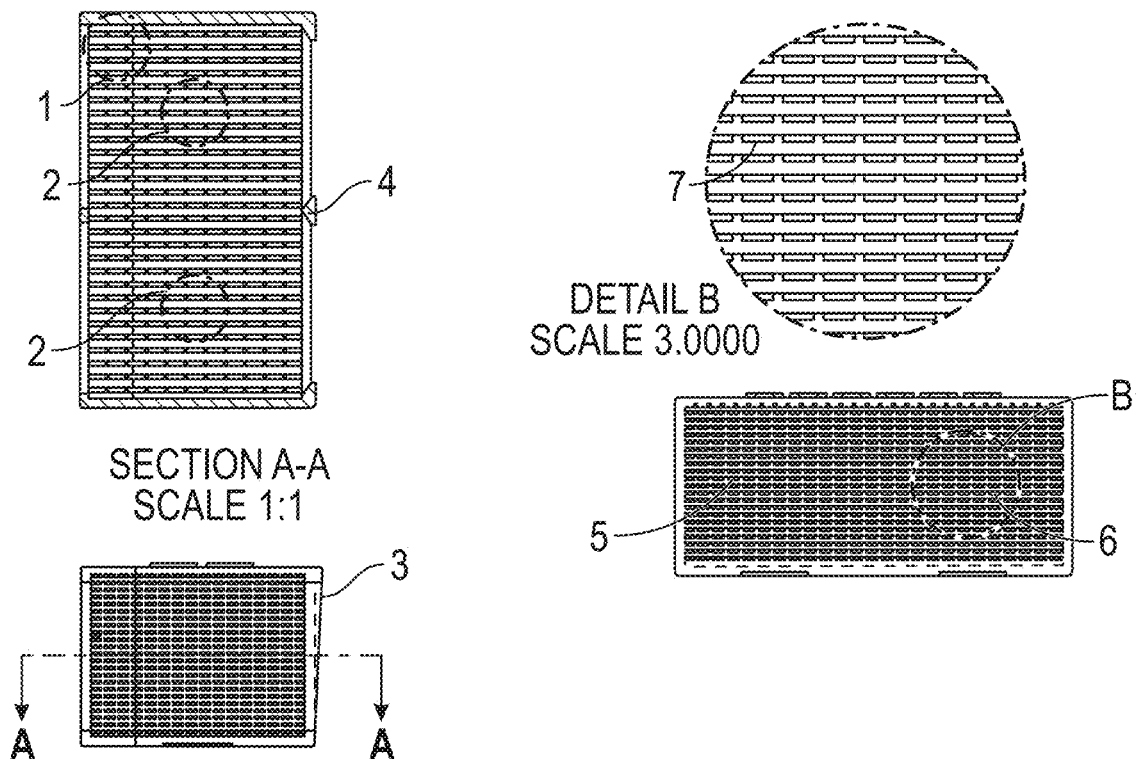
FIG. 10 is a diagram showing the scrubber FRU.

Unique to the Lung is the oxygen canister FRU, as shown at 10 in FIG. 10. A significant advantage over the prior art, the use of recyclable and/or disposable oxygen canisters eliminate the need for oxygen-safe refill and storage and the hazards associated with handling of high pressure oxygen. Another advantage over prior systems is that no license or special certifications are required of the user, both necessary to obtain high pressure oxygen cylinder refills. Another advantage over prior art is that no testing of the gas supply is required by the user, as the content of the canister FRU is assured during manufacturing and is not refillable. The canisters have no external seals to fail, maintain, or collect contamination, and are easy to transport.

Figure 11:
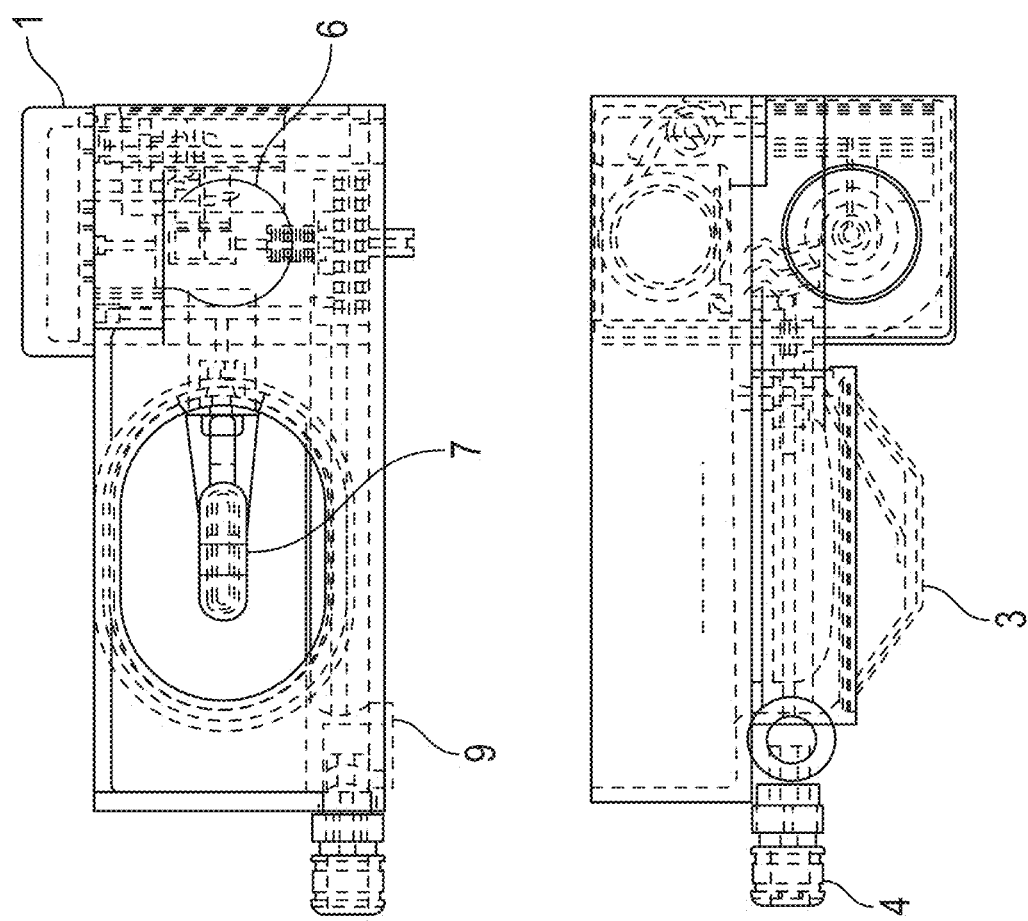
FIG. 11 is a diagram showing the mixing head assembly and the nine major parts.
Figure 12:
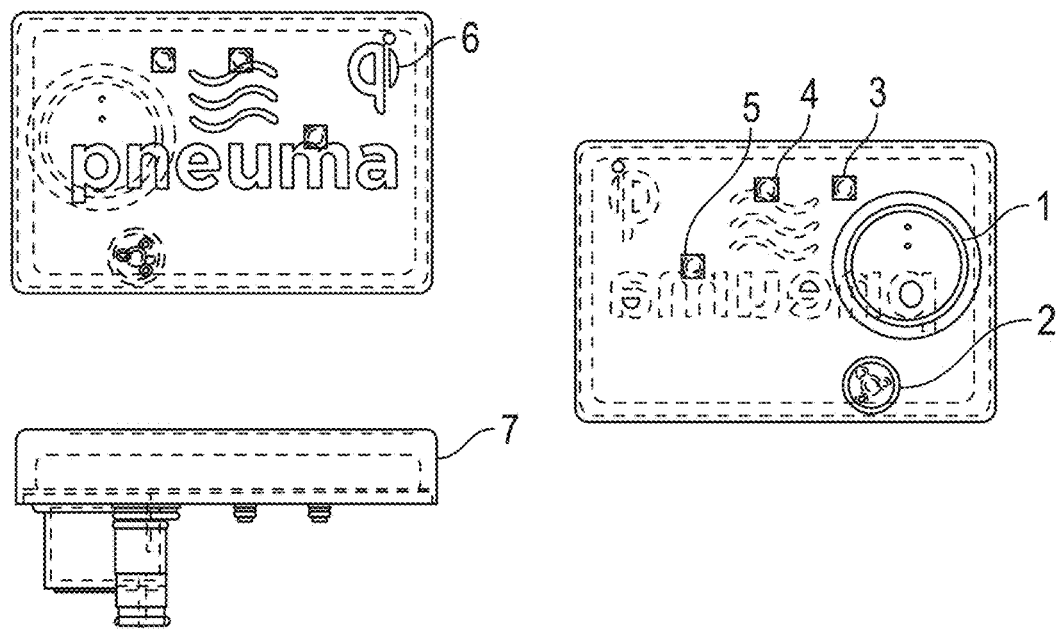
FIG. 12 is a diagram showing the electronics and sensor pod.

The canister is threaded onto the pressure regulator 2 shown in FIG. 11 with the pin 8 pushed into the center of the canister. The pin pushes into the center of the canister fitting as shown at 3, past the enclosed O-ring 2 sealing the connection. Once the canister is secure in the threads, the pin pushes ball valve 1 opening the canister valve to the regulator. The thread connecting the oxygen canister to the pressure regulator 4 does not have a seal, and the canister need not be connected tightly. The RFID Tag on the oxygen canister rotates with the canister and registers with the REID antenna located in the mixing chamber 1 at the location shown in FIG. 13, validating the installation and use. An advantage of this design over the prior art is the elimination of external or user maintained seals. Another advantage over the prior art is the elimination of external or user controlled valves. In the prior art devices, these valves can be accidentally turned-off or not turned-on. The fail-safe design of the maximum and minimum $PPO_2$ removes the need for the user to turn the oxygen valve off while in use, even if the oxygen injector valve were to stick open.

A novel diluant gas bladder is located at 11 in FIG. 2 and is connected to a fitting 19 and the pressure regulator 2 shown in FIG. 11. This bladder provides the air required to the diluant valve 2 shown in FIG. 2 and 7 in FIG. 11. An advantage over the prior art is that this bladder is soft, collapsible and transportable by common carriers when deflated. Before use, the bladder is inflated with air by the user and a hand pump. The hand pump is attached to the air quick fitting shown at 4 in FIG. 11.

Figure 17:
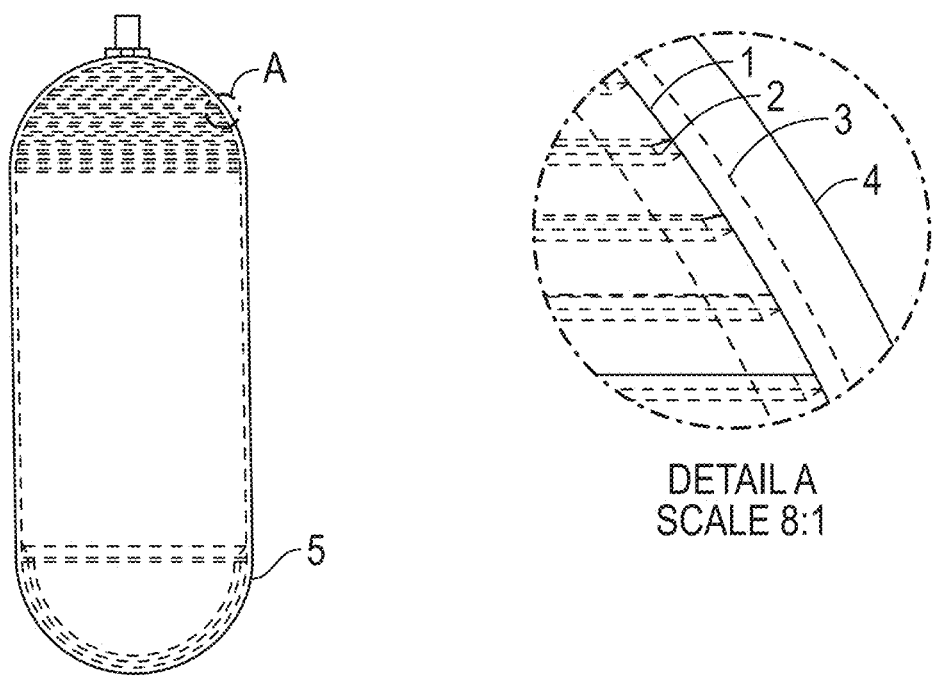
FIG. 17 is a diagram showing the diluent bladder.
Figure 18:
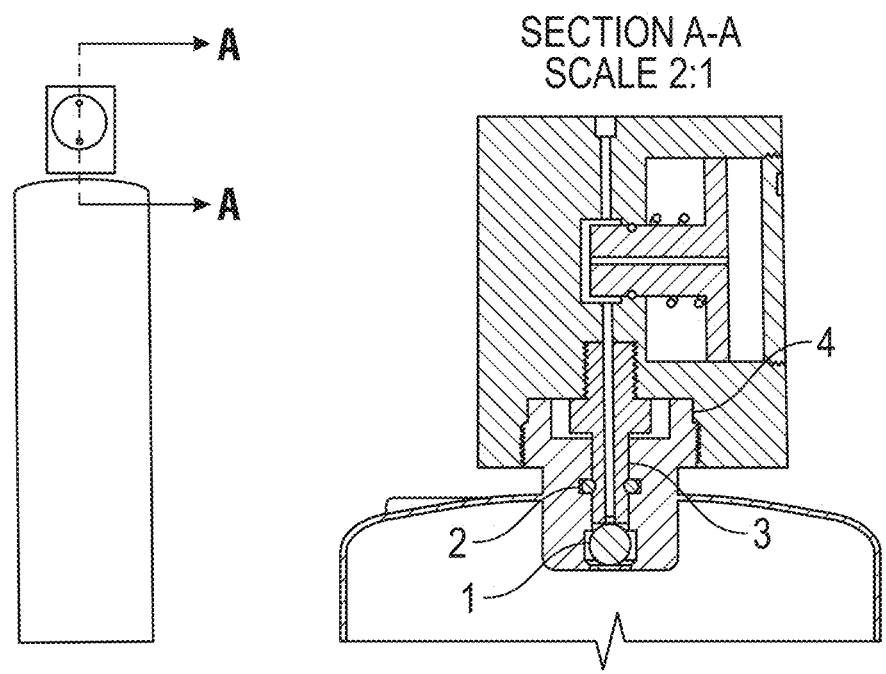
FIG. 18 is a diagram showing the Oxygen FRU valve.
Figure 19:
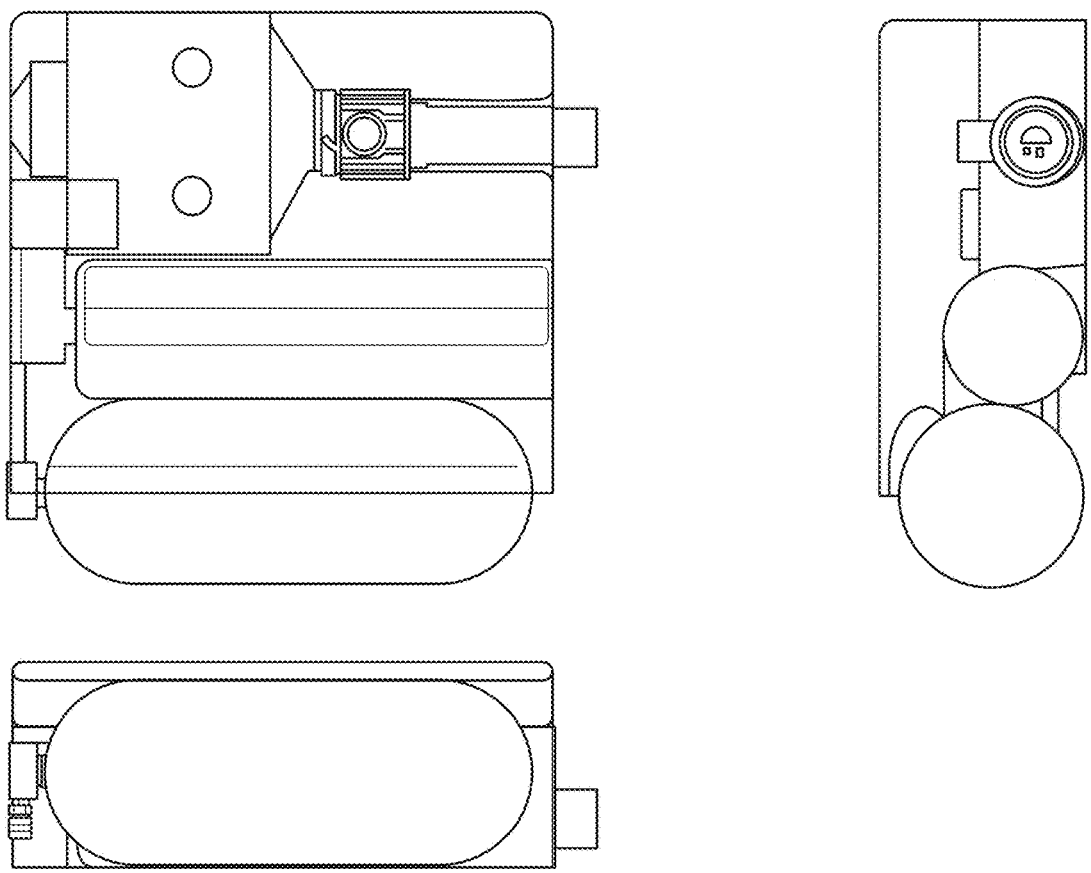
FIG. 19 is a diagram showing the assembly of the Pneuma system.
Figure 20:
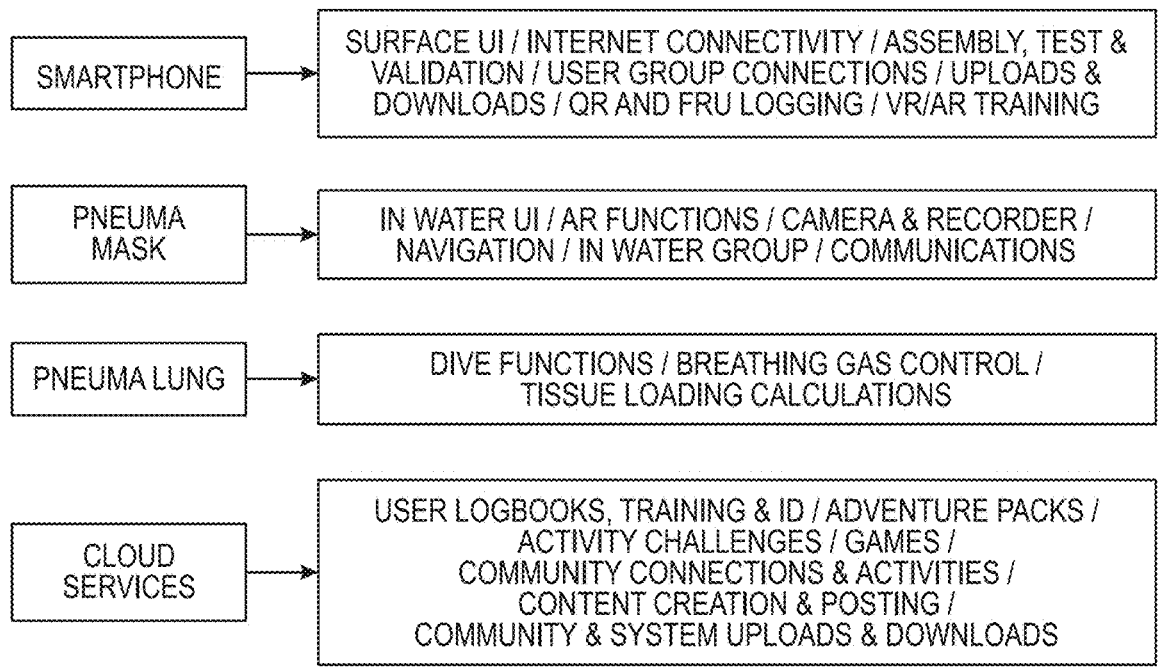
FIG. 20 is a flowchart of the distributed functions of the Pneuma system.
Figure 21:
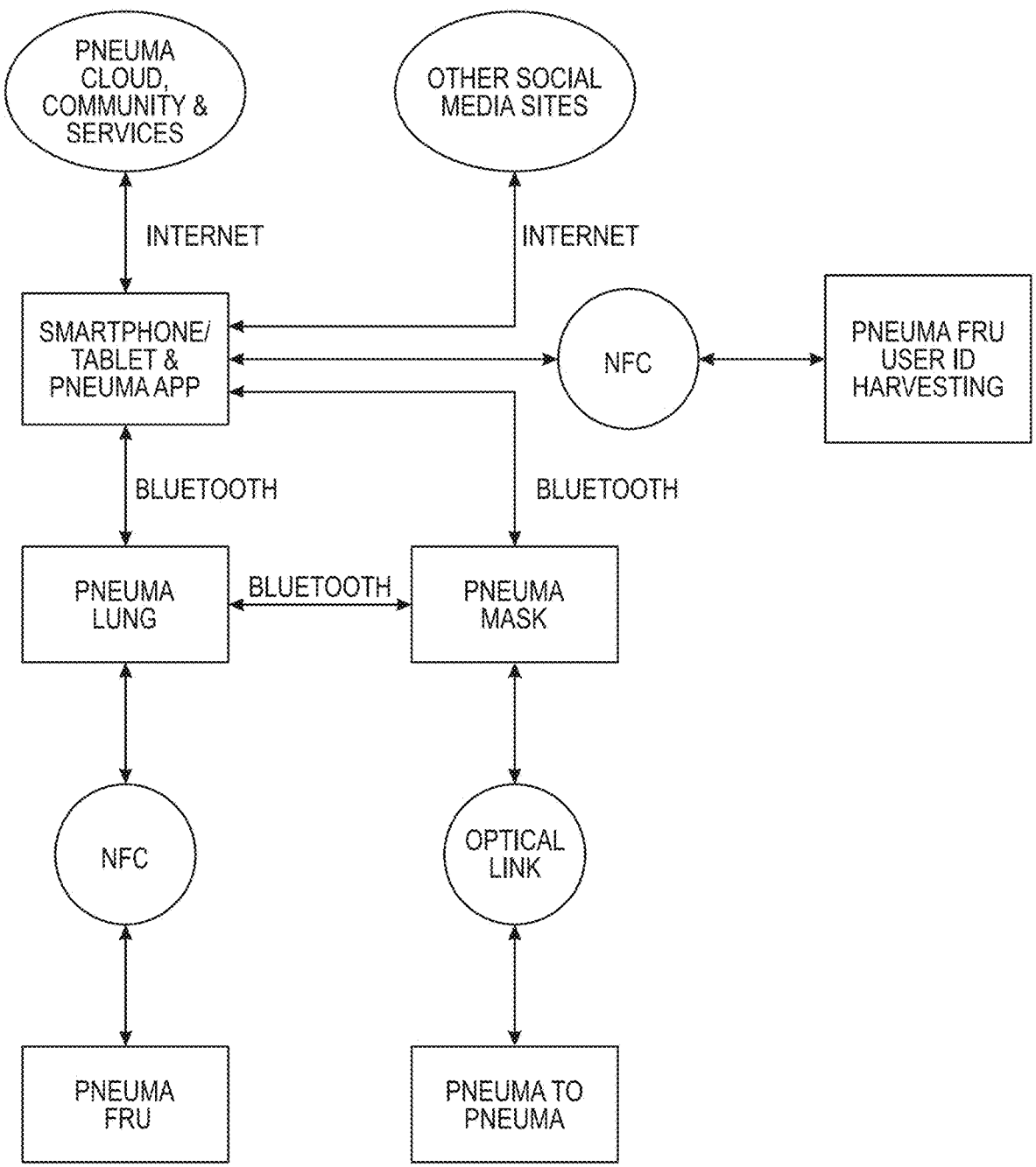
FIG. 21 is a flowchart of the communications paths.

The bladder is unique in design, made multiple layers of fabric and a metallic cap on the top of the bladder, as shown at 1 in FIG. 17. The cap has a threaded fitting at the end to attach to the Lung and circumferential notches in the outer surface as shown at 2 in FIG. 17. The current embodiment has an inner liner of Dacron fabric, shown at 3 in FIG. 17, coated with a gas tight inner polyvinyl coating. This coating is mechanically and chemically bonded to the metallic cap and the circumferential notches. The bottom of the bladder is layered with three more layers of liquid-crystal polymer fabric bonded to the Dacron, as shown at 5 in FIG. 17. The entire bladder is then over-wrapped with another layer of liquid-crystal polymer threads, as shown at 4 in FIG. 17.

The Lung uses an novel method to approximate and track carbon dioxide gas absorption of the scrubber cartridge. This method is an improvement over the prior art as it needs no dedicated sensors to estimate scrubber remaining capacity. Carbon dioxide scrubber irregularities in flow patterns, density distribution, and the possibility of a gas breakthrough are well explained in the prior art scrubbers. The FRU scrubber cartridge in the Lung has eliminated the above problems with the novel diffuser, pre-engineered gas flow channels, bi-directional dual scrubber ports, predetermined capacity, the protective housing, and the Tag memory.

As detailed elsewhere in this disclosure, the chemical used to form the scrubber gas channels has a deterministic capacity to absorb carbon dioxide gas in the stated conditions. We know the human body is not capable of converting oxygen to carbon dioxide at the rate greater than 1:1 of the oxygen metabolized, and most of the time this conversion rate is less. If we use a constant of 1:1 ratio of oxygen to $CO_2$, we are conservative. While it is possible for the user's respiration tidal volume rates to exceed the capacity of the scrubber dwell times, the differential sensor in the Lung can be used to detect this.

Figure 28:
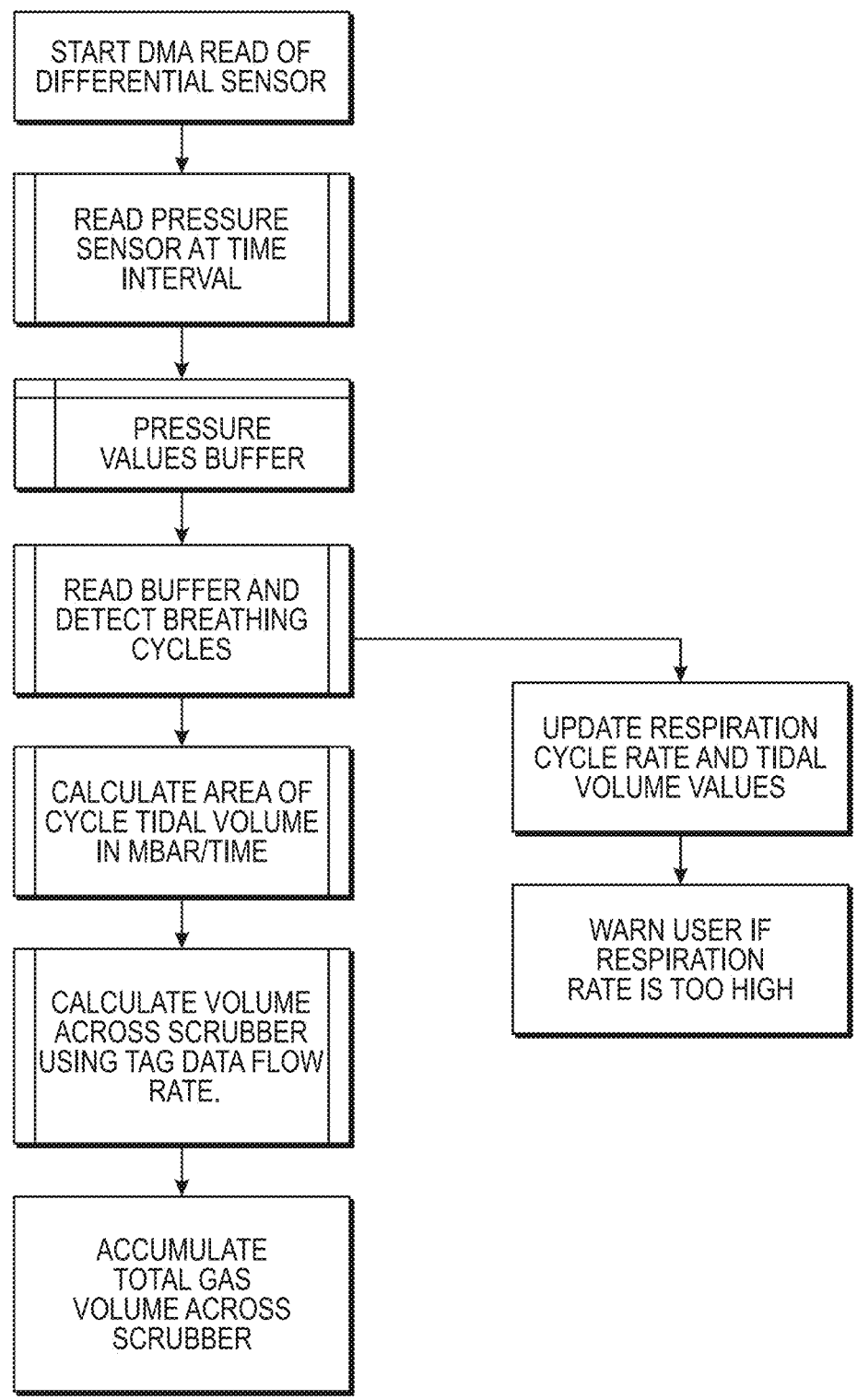
FIG. 28 is a flowchart of the respiration volume calculation.

The novel method of the current embodiment integrates the known capacity of the scrubber chemical from the scrubber FRU Tag data, the known amount of oxygen injected into the breathing loop from the volume of oxygen injected by the oxygen valve, and the oxygen cartridge Tag data. Since the oxygen pressure regulator is balanced to the pressure in the mixing chamber, Bernoulli's equation will give gas volume over time for the valve orifice—see flowchart 27. Additional data may be added to the integration using the calculated respiration tidal volume calculated from the differential pressure sensor, as shown in flowchart FIG. 28.

To be fail-safe, the Lung keeps the user with a life sustaining breathing gas at all times, even when the oxygen supply is exhausted or during a malfunction. This requires careful consideration of the oxygen partial pressure maintained in the unit. With no changes to the loop percent of oxygen, the partial pressure of oxygen ($PPO_2$) will increase as the user descends into the water. With no changes to loop percent of oxygen, the $PPO_2$ will decrease as the user ascends. The current embodiment assures the user has sufficient $PPO_2$ for a rapid accent with no further oxygen injections (in case of an empty oxygen cartridge), as well as assures the user will not have an excess of $PPO_2$ and a central nervous system (CNS) event if the oxygen valve 7 in FIG. 12 were to stick open during a rapid descent. Accepted dive medical standards specify a minimum 0.16 $PPO_2$ must be maintained to safely sustain life. The same standards specify 1.6 $PPO_2$ should not be exceeded to prevent a CNS toxicity event. The Lung design and software assures the $PPO_2$ in the loop at the surface will not result in a $PPO_2$ greater than 1.6 during a rapid or uncontrolled descent, and the $PPO_2$ at the maximum depth of 20 meters will not result in a $PPO_2$ less than 0.16 at the surface during a rapid or uncontrolled accent.

In the current embodiment, the breathing loop is maintained at a $PPO_2$ of 0.21 at the surface. In the current embodiment, at the maximum operating depth for the Lung, the software maintains the loop $PPO_2$ at a maximum of 0.63 and a minimum $PPO_2$ of 0.48 in order to have the 0.16 minimum at the surface.

In the current embodiment, the maximum injection rate of the oxygen valve 2 shown in FIG. 12 is 1.5 liters per minute. The current design as has about five liters of loop volume. If the oxygen injection valve were to fail in the open position, the increase in PPO2 would be less than 33% per minute (due to venting of the loop volume). Recreational scuba standards recommend a maximum accent rate of 20 meters per minute. With a $PPO_2$ of 0.63 at 20 meters, the user will have 2.5 to 3 times the recommend limit to respond to the visual warnings and ascend to 5 meters or less before the $PPO_2$ reaches the 1.6 maximum. Each meter of decrease in depth the user ascends extends this time.

Figure 25:
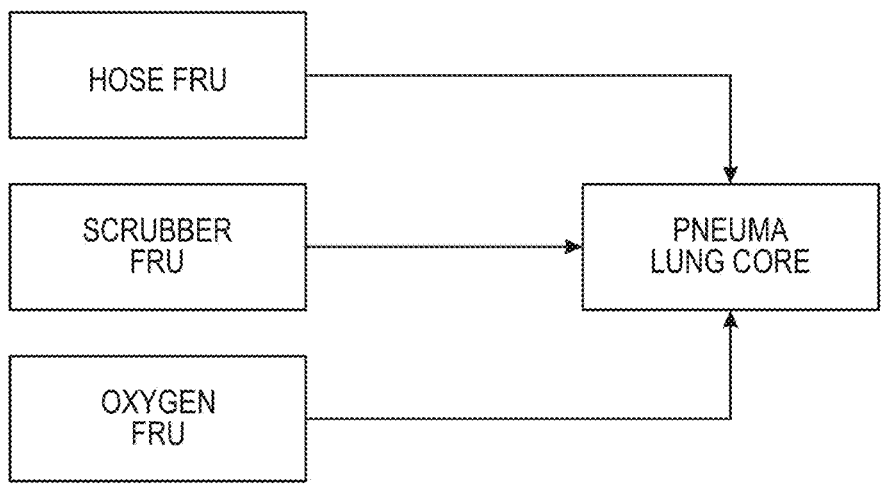
FIG. 25 is a flowchart of the three FRU's of the Lung.

A novel improvement over the prior art is the design and use of user field replaceable units (FRU) for the breathing loop components, carbon dioxide scrubber, and oxygen supply as shown in FIG. 25 and in locations 4, 7, and 10 as shown in FIG. 2. This is further improved by embedding a secure electronic memory (Tag) in each FRU to record and subsequently track the manufacturing, test and validation, and use of each FRU through the life cycle of each unit. A further advantage over prior art is the secure encryption of production, test, and use data of each FRU in the Tag memory. This secure data is available for user skill improvement, diagnostics, and post-event investigation and analysis.

The memory device used in each FRU is an energy harvesting design, meaning the memory does not have its own energy source, such as a battery, but rather collects radio frequency energy from the environment, which is then converted and stored in a capacitor. This is advantageous as no battery or external connections are needed, reducing the size, cost, and service life of the device. The memory is secure, having a processor with cryptographic algorithms and sections of one-time programmable memory, read-write memory, and secure keys. In the current embodiment, each Tag is produced with a unique FRU ID number, the FRU part number, manufacture ID, and manufacture data written to the one-time programmable memory of the first block. Each sequential block is also written with a DES security key and CRC, which must be known to write to the block. When each FRU is tested, data formatted for each FRU is written to the third block. This data may then be used by the Lung to understand the parameters of the individual unit. Each time the unit is installed and used, a modified block chain data block is written to sequential sections of the 34 remaining memory pages.

The current embodiment has a type 2 Tag format with 1024 bytes of total storage, a 4 byte unique ID code, and the standard NDEF format. Each Tag has 16 sectors with 64 bytes per sector. The first sector is used to identify the FRU. The second sector is used to store the handoff data for the smart phone app. The NDEF standard uses the last 16 byte block of each sector for the Sector Trailer, 6 bytes for the read security key of that sector, 4 bytes for the access code, and another 6 bytes for the write key security key of that sector. This leaves 640 bytes for user data. Critical data is stored as a Value Block in a modified block chain format and uses an entire 16 byte block for each 4 bit number value. NDEF records have a 6 byte header for each record. Each time stamp in the Tag is stored as the 32 bit Julian date (Unix 1/1/70), using 4 bytes. The data FRU product ID, manufacture date, LOT code, Manufactures and Pneuma URL, FTP handoff data, phone number, and email address in the header.

The current embodiment of the scrubber FRU Tag has the following additional information:
time stamp of current insertion into the Pneuma correctly and user ID (8 bytes);
time stamp of current self-test with test results and ID (12 bytes);
time stamp of start of current dive and ID (8 bytes);
time stamp, average depth, average temp differential, max temp differential, number of respirations, oxygen quantity used, average PPO$_2$ at end of current dive (10 bytes);
time stamp of opening the shipping can and user ID who opened it (8 bytes);
cumulative number of dives (1 byte);
cumulative dive time (4 bytes);
cumulative average depth (1 byte);
cumulative oxygen flow (2 bytes);
cumulative respirations (2 bytes); and
cumulative respiration volume (2 bytes).

Figure 23:
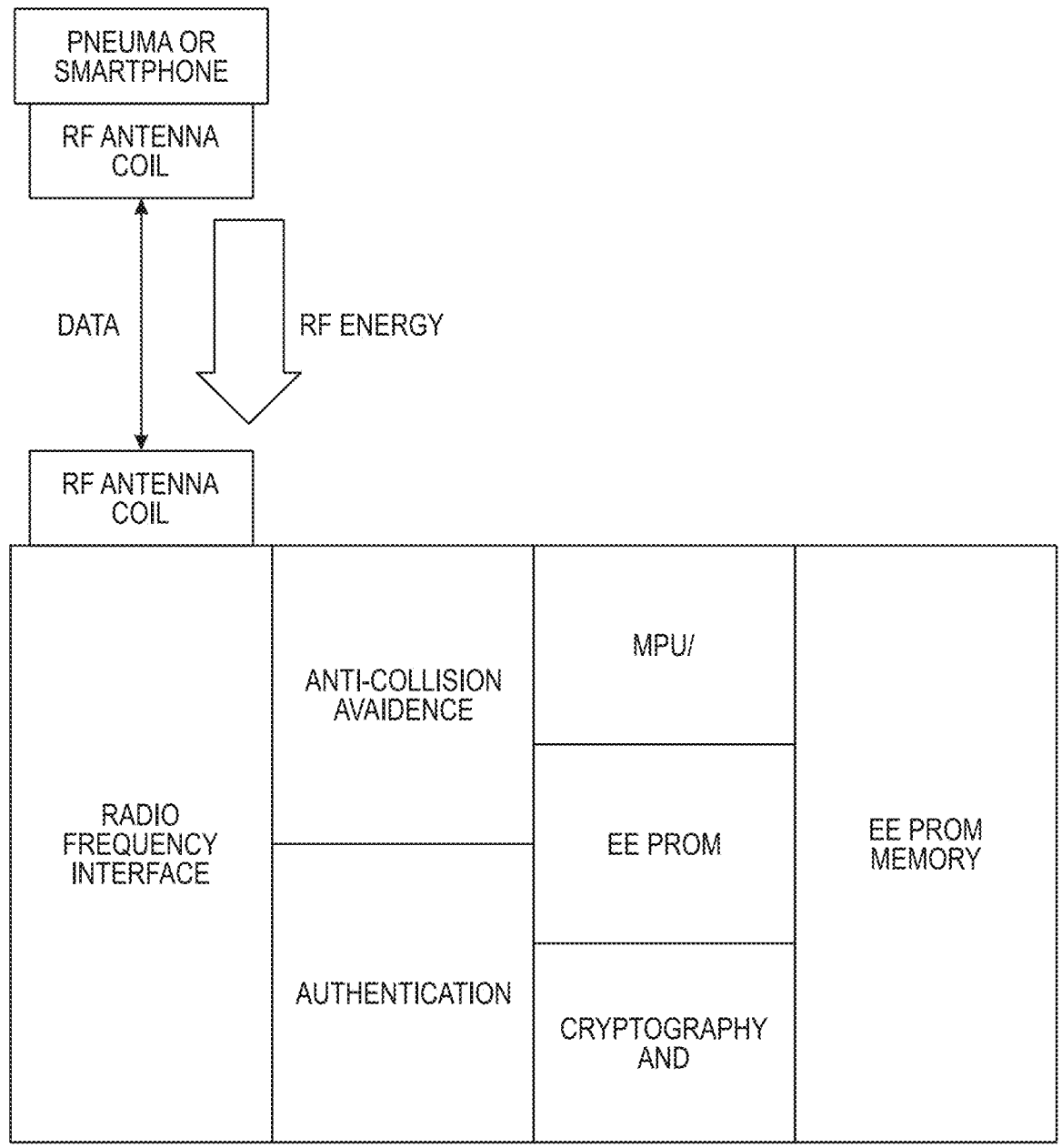
FIG. 23 is a flowchart of the NFC TAG system.

In the current embodiment, each Tag has a NXP Semiconductor MF Series SOT500-4 die with either an 13.56 MHz omni-directional antenna or a tuned 13.56 MHz directional antenna, depending on the placement of the Tag on the FRU. Neither the device selection nor the specific design is intended to be limiting, as other NFC devices will also work. The schematic design of the current embodiment is shown in FIG. 29, with the block diagram of the Tag shown in FIG. 23. This schematic is not intended to be limiting, as other antenna and IC designs will also work.

In the current embodiment, the Tags may be read by the App prior to installation in the Lung to validate the usability of the FRU. The Smartphone or tablet must have a Type II NFC reader to perform this. The current embodiment of the Lung uses an NXP PN532 NFC controller in the electronics pod shown in FIG. 12 connected to two 13.56 MHz antennas located at 4 in FIG. 7 and 1 in FIG. 13.

Humans metabolize oxygen ($O_2$) to create energy, a byproduct of this metabolism is carbon dioxide ($CO_2$). Excessive carbon dioxide in the blood is a condition known as hypercapnia and can, at extreme levels, be fatal. Humans have no mechanism to sense or detect blood oxygen levels. Rather, the body senses $CO_2$ levels to stimulate ventilation or even dyspnea (shortness of breath). Human tolerance for abnormal blood $CO_2$ levels is rather narrow, so this must be managed carefully. When we descend into the water column, pressure increases with a subsequent increase in gas partial pressures, this includes $CO_2$ partial pressure. Gas partial pressure has a close relationship with dissolved gas levels in our body, so if we increase the partial pressure of an inhaled gas, we will increase the dissolved gas level in our body. Increased depth into the water column increases dissolved gas levels in our body. For oxygen, this is managed by adjusting the percentage of oxygen in the breathing gas. For $CO_2$, this increase must be managed and removed from the breathing gas to keep blood-dissolved $CO_2$ in a narrow range.

The $CO_2$ concentration in atmospheric air is about 0.04%. After metabolizing oxygen, our blood can have concentrations up to 0.6%. To allow the exchange of $CO_2$ out of our blood, we must keep the $CO_2$ of our inhaled breath well below this 0.6% value or that transfer will not take place. As we descend into the water, the partial pressure of all gases increase including the $CO_2$ in the inspired air. Pneuma must keep the $CO_2$ partial pressure below 0.06 at all times.

Humans at rest metabolize about 0.25 liters of oxygen a minute, and the byproduct of this is energy and carbon dioxide. The more energy we need, the more oxygen we must consume, creating more $CO_2$. The food we convert to energy affects the rate of $CO_2$ production. Carbohydrates produce about 1000 ml of $CO_2$ for each 1000 ml of oxygen. Fats produce about 720 ml for each 1000 ml of $O_2$. Proteins produce about 800 ml for each 1000 ml of $O_2$. Alcohol produces about 660 ml for each 1000 ml of $O_2$.

Empirical observations have shown divers consume about 800 ml of $O_2$ per minute during a dive, and this can exceed 2000 ml or more when stressed or working hard.

The carbon dioxide scrubber cartridge FRU shown in assembly location 7 in FIG. 2 and in detail in FIG. 10 is unique over prior art gas scrubbers. The cartridge is designed to be fail-safe, easy to install, redundant, and trackable. Prior art scrubbers require special skills to install, maintain, and calculate usage. The Lung scrubber cartridge eliminates the potential for errors using an encased chemical block with pre-engineered gas channels, a shape which cannot be installed in the wrong orientation, conformal seals which do not need service, a positive magnetic retainer system to latch the cartridge into the housing, and an electronic RFID data storage Tag to record manufacturing, test, validation, flow, and usage data.

The scrubber cartridge has pre-formed and pre-engineered gas flow channels in parallel with the length of the cartridge as shown at 7 in FIG. 10. Currently each cartridge has about 1,200 mm2 of gas flow area divided between the exhalation and inhalations sides of the cartridge. The flow of gas through the individual cartridge channels is validated when manufactured, and the flow rate of each cartridge is recorded in the RFID Tag embedded in each cartridge. This testing and recording of cartridge data is used by the software to make calculations of total gas flow through the cartridge during use.

The scrubber chemical in the cartridge is currently Molecular Products Sofnolime 797 Grade provided in granular form, although other brands and formats could be used. Sofnolime 797 has a nominal moisture of 16-20% and absorbs about 150 liters of $CO_2$ per kilogram at Standard Atmosphere (1013 pa at 15° C.). The process of absorbing $CO_2$ gas from respiration is as follows: $CO_2(gas) + H_2O \rightarrow CO_2(solution) + NaOH \rightarrow NaHCO_3 + Ca(OH)_2 \rightarrow CaCO_3 + NaOH + H_2O$.

Carbon dioxide gas is hydrated and combined with sodium hydroxide. This creates an exothermic (heat) reaction and creates sodium bicarbonate. This is mixed with Calcium hydroxide creating calcium carbonate, sodium hydroxide, and water. We then use the sodium hydroxide and water again to regenerate the scrubber.

The absorption chemical is processed by grinding in a powder form, mixed with about 2% polymer binder, then extruded into the channels for the block needed for the cartridge. Depending on respiration rates of the user and the current design of the channels, the scrubber cartridge needs between 36 and 60 $cm^2$ of area to absorb each liter of respired $CO_2$. The current design of the Lung has 30 liters of oxygen, which will metabolize to about 24 liters of $CO_2$. This shows that we need between 864 and 1,440 cm2 of scrubber volume for each 30 liters of oxygen in each oxygen cartridge. The scrubber cartridge in the current disclosure has 2065 $cm^2$ of scrubber combined between the exhalation and inhalation sides. This volume of scrubber chemical is twice what is needed, with each side of the scrubber cartridge providing 100% of the needed capacity to the system.

Fluorescent dye oxygen sensors that may be used with the current embodiment are well known. Examples are provided, without limitation, in the following patent documents that are incorporated herein by reference: GB2479183A, U.S. Pat. Nos. 3,612,866, 4,810,655, 5,030,420, 5,043,286, 5,094,959, 5,718,842, 5,863,460, and 6,664,111.

Historically, prior art rebreather apparatuses have used Clark or electrochemical galvanic type oxygen sensors, with well documented success and failure rates. More recently, fluorescent quench gaseous and dissolved, surface and fiber optic sensors are being developed which meet the requirements of higher oxygen partial pressures needed for dive apparatus.

Utilization of the devices and methods described in above-referenced U.S. patent application Ser. No. 16/409,253 further increase the safety and reliability of any type of oxygen sensor.

In the current embodiment, the Lung has a gaseous fluorescent quenching dye sensor using a strobed 450 nm LED, a polymer membrane with an oxygen quenching ruthenium diimine complex coating, and a monolithic 600 nm photo receptor. Using the Stern-Volmer equation, the quench of the Ru2ClO4 complex is measured as the delta of the strobe decay, then combined with mixing chamber pressure and mixing chamber temperature. This calculation results in an good approximation of the present $PPO_2$ in the mixing chamber.

In the current embodiment, the Lung is self-instructing utilizing software in the App, Mask and Lung; sensors in the Smartphone, Mask and Lung; RFID data from each FRU; QR coded seals on the FRU packages; Services from the cloud; and data collected from prior use of the device.

In the current embodiment, the programed learning App begins with a secure identity validation of each user to assure and confirm the unique identity of each person who may later become authorized to use the Lung. The programed learning methods in the App, along with Services, start by presenting a consistent program of environmental awareness and responsibility, dive theory, dive physiology, Lung and Mask operation, and other training not directly needing the sensors of the Lung and Mask. When appropriate, the programed learning App may seek identity of the QR code on the FRU seal using the Smartphone camera. This is done to positively identify the FRU package to the trainee and to the App. When appropriate, the programed learning App may seek identity of the FRU Tag using the near field radio in the Smartphone. The FRU is identified and validated using, among other data, the production information and usage data stored in the FRU Tag memory.

Using any combination of graphics, text, virtual, and augmented reality, the training App indicates to the trainee how to identify and inspect the FRU for usability and how to install the FRU to the Lung and/or Mask. The RFID sensors in the Mask and/or Lung identify and confirm the FRU is installed correctly and send this data back to the App.

In the current embodiment, this sequence is followed for all three FRU with each FRU Tag read and validated. The diluant pressure is observed, and the App may further instruct the trainee how to add air to the diluant bladder.

The current embodiment device conducts a progressive self-test and validation using the sensors in the Lung, Mask, and Smartphone. The oxygen pressure sensor 5 and the diluant sensor 4 shown in FIG. 12 are read prior to the installation of the oxygen canister FRU and compared to each other and the pressure sensor in the Smart-phone. After the oxygen FRU is installed, the oxygen pressure sensor is read again to validate the sensor and the FRU. While the diluant bladder is inflated, the diluant pressure sensor is validated. The loop pressure sensor 3 in FIG. 12 is read and validated by the trainee and the pressure sensor in the Smartphone. The oxygen sensor is read prior to the installation of the scrubber FRU and is validated to the oxygen content of the ambient air. After the scrubber FRU and Oxygen FRU are installed, the calibration shutter 7 in FIG. 16 is closed, and the current to activate the shutter is measured by the electronics pod. The oxygen injector valve 2 in FIG. 12 is opened, and the current used by the valve is measured by the electronics pod. The oxygen sensor and the oxygen injector are then validated using the expected rise in oxygen partial pressure in the oxygen sensor well. Once the oxygen partial pressure reading has stabilized, the oxygen sensor is calibrated using the routine detailed elsewhere in this disclosure. At some point after a sequence of validations, the App instructs the trainee to breathe through the Lung using the Mask. The differential pressure sensor 10 FIG. 9 and the loop pressure sensor 3 in FIG. 12 detect the breathing cycle of the trainee along with pressure changes in the breathing loop, validating the integrity of the breathing loop.

In the water, the current embodiment of the training software recommends gamified skill building exercises, while displaying recommended operation limits. The self-teaching software is able to make recommendations for the trainee from the dive log data to improve skills and challenge the trainee to pursue advanced skills. Connectivity with the cloud Services connects the user with the programed learning community and provides reinforcement and encouragement of skill building. The App sets limits on each individual trainee and sets recommended limits to the use of the device based on demonstrated mastery of prior skills.

The principle and mode of operation of this invention have been explained and illustrated in its preferred embodiments. However, it must be understood that this invention may be practiced otherwise than as specifically explained and illustrated without departing from its spirit or scope.

What is claimed is:

1. A rebreather apparatus comprising;
a closed loop respirator including a plurality of components; and
a device that communicates with two or more of the plurality of components of the closed loop respirator and, using information received from and regarding the two or more of the plurality of the plurality of components, performs a self-training application for a user of the closed loop respirator and thereby provides the user with self-training in the proper assembly and operation of the closed loop respirator.

2. The rebreather apparatus of claim 1 wherein the self-training application uses two or more of:
   (1) sensors in the closed loop respirator;
   (2) augmented reality images and real sensors data from the closed loop respirator;
   (3) augmented reality images in a smart phone device and sensors data from the closed loop respirator;
   (4) augmented reality images in a dive mask and sensors data from the closed loop respirator;
   (5) RFID to identify specific re-charge units;
   (6) RFID to assess correct apparatus assembly;
   (7) augmented reality object recognition to identify re-charge units; and
   (8) augmented reality object recognition to assess correct apparatus assembly.

3. The rebreather apparatus of claim 1 wherein the self-training application teaches the installation and removal of user installed re-charge units.

4. A rebreather apparatus comprising:
a closed loop respirator;
two or more components including:
   (1) a mask that includes augmented reality displays incorporated therewith that provide a self-training application;
   (2) a mask and a portable computing device, wherein sensors for the rebreather apparatus are distributed among two or more of the respirator, mask, and portable computing device;
   (3) smart-phone enabled operation;
   (4) one or more re-charge units that are removable and replaceable by a user of the closed loop respirator;
   (5) one or more directional RFID antennas adapted to detect respirator component location and/or orientation;
   (6) a disposable hose and counter-lung;
   (7) disposable one-way valves;
   (8) two counter-lung chambers using a common wall;
   (9) a single-unit dual counter-lung;
   (10) hydrogel in the closed loop respirator to immobilize liquids;
   (11) a breathing mask, a counter-lung, and a coaxial hose providing fluid communication between the breathing mask and counter-lung;
   (12) a disposable conformal seal in the closed loop respirator;
   (13) a taper conformal seal in the closed loop respirator;
   (14) a water-trap;
   (15) an integrated surface supply snorkel;
   (16) a convergent duct on an inhalation side of a carbon dioxide scrubber;
   (17) a divergent duct on an exhalation side of a carbon dioxide scrubber; and
   (18) a differential pressure sensor on each of exhalation and inhalation sides of the closed loop respirator; and
a device that communicates with the two or more of the components and, using information received from and regarding the two or more of the plurality of the plurality of components, performs self-training application for a user of the closed loop respirator and thereby provides the user with self-training in the proper assembly and operation of the closed loop respirator.

5. The rebreather apparatus of claim 4 wherein a convergent duct is provided on an inhalation side of a carbon dioxide scrubber, and wherein the carbon dioxide scrubber includes an RFID memory device storing unique identification data.

6. The rebreather apparatus of claim 5 wherein the carbon dioxide scrubber includes an RFID memory device storing unique identification and use data.

7. The rebreather apparatus of claim 5 wherein a scrubber cartridge of the carbon dioxide scrubber includes RFID validation of installation.

8. The rebreather apparatus of claim 5 wherein a carbon dioxide scrubber chemical is enclosed in a scrubber cartridge of the carbon dioxide scrubber.

9. The rebreather apparatus of claim 8 wherein the scrubber cartridge of the carbon dioxide scrubber is a dual port scrubber cartridge.

10. The rebreather apparatus of claim 8 wherein the scrubber cartridge of the carbon dioxide scrubber is a bi-directional scrubber cartridge.

11. The rebreather apparatus of claim 8 wherein the scrubber cartridge of the carbon dioxide scrubber includes a magnetic latch.

12. The rebreather apparatus of claim 8 wherein the scrubber cartridge of the carbon dioxide scrubber includes a tapered conformal seal.

13. The rebreather apparatus of claim 8 wherein the scrubber cartridge of the carbon dioxide scrubber includes flow channels in the scrubber material.

14. A rebreather apparatus comprising;
a closed loop respirator including a plurality of components; and
a smartphone or tablet computer that communicates with two or more of the plurality of components of the closed loop respirator and, using information received from and regarding the two or more of the plurality of the plurality of components, performs a self-training application for a user of the closed loop respirator and thereby provides the user with self-training in the proper assembly and operation of the closed loop respirator.

* * * * *